(12) United States Patent
Tuan et al.

(10) Patent No.: US 6,395,549 B1
(45) Date of Patent: May 28, 2002

(54) LONG TERMINAL REPEAT, ENHANCER, AND INSULATOR SEQUENCES FOR USE IN RECOMBINANT VECTORS

(75) Inventors: Dorothy Tuan, Martinez, GA (US); Qiaoming Long, Ottawa (CA); Chikh Bengra, Charlottesville, VA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 09/422,576

(22) Filed: Oct. 21, 1999

Related U.S. Application Data

(60) Provisional application No. 60/105,256, filed on Oct. 22, 1998.

(51) Int. Cl.$^7$ .................. C12N 15/63; C12N 15/09; C07H 21/04; C12P 21/06

(52) U.S. Cl. ............... 435/455; 435/320.1; 435/69.1; 435/325; 536/24.1

(58) Field of Search .................. 424/93.21; 514/44; 435/320.1, 69.1, 455, 325; 536/23.1, 24.1

(56) References Cited

U.S. PATENT DOCUMENTS

| | | |
|---|---|---|
| 5,710,037 A | 1/1998 | Vanin et al. |
| 5,744,133 A | 4/1998 | Lathe et al. |
| 5,753,499 A | 5/1998 | Meruelo et al. |
| 5,756,264 A | 5/1998 | Schwarz et al. |
| 5,759,852 A | 6/1998 | Kirschner et al. |
| 5,770,400 A | 6/1998 | Miyazaki et al. |
| 5,783,442 A | 7/1998 | Kato et al. |
| 5,789,244 A | 8/1998 | Heidrun et al. |
| 5,795,577 A | 8/1998 | Kieny et al. |
| 5,811,260 A | 9/1998 | Miyazaki et al. |
| 5,814,482 A | 9/1998 | Dubensky, Jr. |
| 5,817,492 A | 10/1998 | Saito et al. |
| 5,830,727 A | 11/1998 | Wang et al. |
| 5,837,503 A | 11/1998 | Doglio et al. |
| 5,856,152 A | 1/1999 | Wilson et al. |
| 5,858,744 A | 1/1999 | Baum et al. |
| 5,866,411 A | 2/1999 | Pedersen et al. |
| 5,866,696 A | 2/1999 | Carter et al. |
| 5,871,997 A | 2/1999 | Rother et al. |
| 5,886,166 A | 3/1999 | Pedersen et al. |
| 5,888,767 A | 3/1999 | Dropuli et al. |
| 5,888,820 A | 3/1999 | Dalla-Favera et al. |
| 5,925,565 A | 7/1999 | Berlioz et al. |
| 5,932,210 A | 8/1999 | Gregory et al. |
| 5,965,358 A | 10/1999 | Carrion et al. |
| 5,965,440 A | 10/1999 | Reeves |
| 5,968,735 A | 10/1999 | Stein et al. |

OTHER PUBLICATIONS

Dang et al. Clin. Cancer Res. 5:471–474, 1999.*
Gerson, S. L. Nature Med. 5:262–264, 1999.*
Wivel & Wilson. Hematol. Oncol. Clin. North Am. 12:483–501, 1998.*
Eck & Wilson. Gene–based therapy in Goodman & Gilman's The pharmacological basis of therapeutics, Ninth edition, pp. 77–101, 1996.*
Bell, A.C. et al., "The Protein CTCF Is Required for the Enhancer Blocking Activity of Vertebrate Insulators," *Cell*, vol. 98, 387–396 (Aug. 1999).
Long, Q. et al., "A Long Terminal Repeat of the Human Endogenous Retrovirus ERV–9 is Located in the 5' Boundary Area of the Human β–Globin Locus Control Region," *Genomics*, 54:542–555 (1998).
Potts, W. et al., Chicken Human β–Globin 5'HS4 Insulators Function to Reduce Variability in Transgenic Founder Mice, *Biochem. & Biophys. Res. Comm.*, 273:1015–1018 (2000).
Zhong, X et al., An Enhancer–Blocking Element Between α and δ Gene Segments Within the Human T Cell Receptor α/δ Locus, *Proc. Natl. Acad. Sci., USA,*, vol. 94: 5219–5224 (May 1997).
Anagnou, et al., Sequences Located 3' to the Breakpoint of the Hereditary Persistence of Fetal Hemoglobin–3 Deletion Exhibit Enhancer Activity and Can Modify the Developmental Expression of the Human Fetal Aγ–Globin Gene in Transgenic Mice. *J. Biol. Chem.* 270:10256–10263 (1995).
Baralle, et al., "The primary structure of the human ε–globin gene," *Cell* 21:621–626 (1980).
Anderson, et al., "Comparative analysis of LTRs of the ERV–H family of primate–specific retrpvirus–like elements isolated from Marmoset, African Green Monkey, and man," *Virology* 234:14–30 (1997).
Ashe, et al., "Intergenic transcription and trasinduction of the human β–golbin locus," *Genes & Dev.* 11:2494–2509 (1997).
Bl, et al., "DNA binding specificity of the CCAAT–binding factor CBF/NF–Y," J. Bio., Chem. 272:26563–26572 (1997).
Blaese & Anderson, "The ADA Human Gene Therapy Clinical Protocol," Hum. Gene Ther. 1:327–329 (1990).

(List continued on next page.)

*Primary Examiner*—Dave T. Nguyen
*Assistant Examiner*—Quang Nguyen
(74) *Attorney, Agent, or Firm*—Charles W. Calkins, Esq.; Cynthia B. Rothschild, Esq.; Kilpatrick Stockton LLP

(57) ABSTRACT

Disclosed are an enhancer, insulator, and promoter from the HS5 region in the 5' boundary area of the locus control region of human β-like globin genes. These transcription control sequences can be used to control expression of any desired gene of interest and can be used in any vector for this purpose. The control sequences are derived from the area in and around the U3 region of a solitary endogenous retrovirus (ERV) 9 long terminal repeat (LTR). Also disclosed are methods of expressing any gene of interest. For this purpose, the control sequences can be operably linked to the gene of interest (and operably linked to each other). The disclosed enhancers, insulators, and promoters can also be used with any other control sequences. Preferably, the control sequences are used in vectors to obtain expression of a gene of interest in a cell, including cells in animals.

36 Claims, 17 Drawing Sheets

OTHER PUBLICATIONS

Buchschacher, et al., "Human innunodoficiency Virus vectors for inducible expression of foreign genes," J. Viral. 66:2731–2739 (1992).

Bukrinsky, et al., "Active nuclear import of human immunodeficiency virus type 1 preintegretion complexes," Proc. Natl. Acad. Sci. U.S.A. 89:6580–6584 (1992).

Chung, et al., "A 5'element in the chicken β–globin domain serves as a insulator in human erythroid cells and protects against position effect in Drosophila," Cell 74:505–514 (1993).

Dicristofano, et al., "Characterization and genomic mapping of the ZNF80 locus: expression of this zing–finger gene is driven by a solitary LTR of ERV9 endogenous retroviral family," Nucleic Acids Research 23:2823–2830 (1995).

Dicristofano, et al., "Mobilization of an ERV9 Human Endogenous Retroviral Element during Primate Evolution," Virology 213:271–275 (1995).

Efstratiadis, et al., "The structure and evolution of the human β–globin gene family," Cell 21:653–668 (1980).

Cavallesco & Tuan, "Modulatory subdomains of the HS2 enhance differentially regulate enhancer activity in erythroid cells at different developmental stages," Blood Cells, Molecules and Diseases 12:8–26(1997).

Chatterjee, etr al., "Dual–target inhibition of HIV–1 in Vitro by means of an adeno–associated virus antisense vector," Science 2581:1485–1488 (1992).

Crossley, et al., "Isolation and characterization of the cDNA encoding BKLF/TEF–2 a major CACCC–box–binding protein in erythroid cells and selected other cells," Mol. Cells. Biol. 16:1695–1705 (1996).

Dhar, et al., "Erthroid–specific nuclease–hypersensitive sites flanking the human β–globin domaine," Mol. Cell. Biol. 10:4324–4333 (1990).

Doolittle & Sapienza, "Selfish genes, the phenotype paradigm and genomic evolution," Nature 284:601–603 (1980).

Efstratiadis, et al., "The structure and evolution of the human β–globin gene family." Cell 21:653–668 (1980).

Grossman, et al., "Successful ex vivo gene therapy directed to liver in a patient with familial hypercholesterolaemia," Nat. Genet. 6(4):335–41 (1994).

Feuchter, et al., "Strategy for Detecting Cellular Transcripts Promoted by Human Endogenous Long Terminal Repeats: Identification of a Novel Gene (CDC4Lease) with Homology to Yeast CDC4," Genomics 13:1237–1246 (1992).

Forrester, et al., "Evidence for a locus activating region: the formation of developmentally stable hypersensitive sites in globin–expressing hybrids," Nucl. Acids Res. 15:10159–10177 (1987).

Golemis, et al., "Alignment of U3 Region Sequences of Mammalian Type C Virusis: Identification of Highly consrved motifs and impications for enhancer design," Journal of Virology 64:534–542 (1990).

Goodchild, et al., Human endogienous long terminal erpeat provides a polyadenylation signal a novel, alternatively spliced transcript in normal placenta. Virology 21:287–294 (1992).

Grosveld, et al., "Position–independent, high–level expression of the human β–globin gene in tragenic mice," Cell 51:975–985 (1987).

Hardison, et al., "Locus Control Regions of Mammalian β–globin gene cluster: combining phylogenetic analysis and experimental results to gain functional insights," Gene 205:73–94 (1997).

Henikoff, et al., "Gene families: The taxonomy of protein paralogs and chimeras," Science 27B:609–614 (1997).

Henthorn, et al., "A gene deletion ending within a complex array of repeated sequences 3' to the human β–globin gene cluster," Proc. Natl. Acad. Sci. USA 83:5194–5198 (1986).

Lamantia, et al., "Identification and characterization of novel human endogenous retroviral sequences preferentially expressed in undifferentiated embryonal carcinoma cells," Nucleic Acids Research 19:1513–1520 (1991).

Lamantia, et al., "Identification of new human repetitive sequences: characterization of the corresponding cDNAs and their expression in embryonal carcinoma cells," Nucleic Acids Research 17:5913–5920 (1989).

Jarman & Higgs, "Nuclear scaffold attachment sites in the human globin gene complese," EMBO J. 7:3337–3344 (1988).

Johnson & McKnight, "Eukaryotic transcriptional regulatory proteins," Annual Rev. Biochem. 58:799–739 (1989(.

Kellum & Schedl, "A position–effect assay for boundaries of higher order chromosomal domains," Cell 64;941–950 (1991).

Kesher, et al., "Mouse retrotransposons: a cellular resservoir of long terminal repeat (LTR) elements with diverse transcriptional specificitis," Adv. Cancer Res. 56:215–251 (1991).

Khoury & Gruss, "Enhancer elements," Cell 33(2):13–4 (1983).

Ko & Engel, "DNA–binding specificities of the GATA transcription factor family,"Mol. Cell. Biol. 13:4011–4022 (1993).

Kong, et al., "Transcription of the HS2 enhancer toward a cis–linked gene is independent of the orientation, position, and distance of the enhancer relative to the gene," Mol. Cell. Biol. 17:3955–3965 (1997).

Lamantia, et al., Identification of regulatory elements within the minimal promoter region of the human endogenous ERV9 proviruses: accurate transcription initiation is controlled by an Inr–like element. Nucleic Acids Research 20:4129–4136 (1992).

Lania, et al., "Structural and functional Organization of the Human Endogenous Retroviral ERV9 Sequences," Virology 191:464–468 (1992).

Li, et al., "Nucleotide sequence of 16 kilobase pairs of DNA 5' to the human β–globin gene," J. Biol. Chem. 260:14901–14910 (1985).

Li, & Stamatoyannopoulos, "Hypersensitive site 5 of the human β Locus Control Region functions as a chromatin insulator," Blood 84:1399–1401 (1995).

Long, et al., "Nucleotide sequence and transcriptional analysis of DNA upstream of hypersensitive site 4 in the human β–globin locus control region," Blood 86:472a (1995).

Long, et al., "Homo sapiens beta–globin locus control region, 5' sequence," Database Genbank "Online" Sequence AF064190 Feb. 2, 1999.

Long, et al., "A long terminal repeat of the human endogenous retrovirus ERV–9 is located in the 5' boundary area of the human –globin locus control region," Genomics 54:542–555 (1998).

Lenz, et al., "Determination of the leukaemogenicity of a muring retrovirus by sequences within the long terminal repeat," Nature 308:467–470 (1984).

Lewis, et al., "Human immunodeficiency virus infection of cells arrested in the cell cycle." EMBO. J. 11:3053–3058 (1992).

Lower, et al., "The viruses in all of us: Characteristics and biological significance of human endogenous retroviruses," Proc. Natl. Acad. Sci. USA 93: 5177–5184 (1996).

Schulte, et al., Human trophoblast and choriocarcinoma expression of the growth factor pleiotrophin attributable to germ–line insertion of an endogenous retrovirus. *Proc. Natl. Acad. Sci. USA* 93:14759–14764 (1996).

Shen, et al., "A history of the human fetal globin gene duplication," *Cell* 26:191–203 (1981).

Orkin, "GATA–binding transcription factors in hematopoietic celllls." Blooed 80:575–581 (1992).

Poncz, et al., "Nucleotide sequence analysis of the δβ–globin gene region in human," J. Biol. Chem. 258:11599–11609 (1983).

Poznansky, et al., "Gene trasfer into human lymphocytes by a defective human immunodeficiency virus type 1 vector," J. Virol. 65(1):532–5 (1991).

reik, et al., "The locus control region is necessary for gene expression in the human globin locus but not the maintenance of an openm chromatin structure in erythroid cells," Molecular and Cellular Biology 18:5992–6000 (1998).

Sanger, et al., "DNA sequencing with chain–terminating inhibitors,"Proc. Natl. Acad. Sci. USA 74:5453–5487 (1977).

Strazzullo, et al., "Characterization and genomic mapping of chimeric ERV9 endogenous retroviruses–host gene transcripts," *Gene* 206:77–83 (1998).

Strazzullo, et al., "Mutational Analysis of the Human Endogenous ERV9 Proviruses Promoter Region," *Virology* 200:686–695 (1994).

Speck, et al., "Mutation of the core or adjacent LVb elements of the Monioney murine leukemia virus enhancer alters disease specificity ," Genes & Development 4:233–242 (1990).

Stavenhagen & Robins, "Ana ancient prvirus has imposed endrogen regulation on the adjacent mouse sex–limited protein gene, "Cell 55:247–254 (1988).

Stief, et al., "Anuclear DNA–attachment element mediates elevated and position–independent gene activity," Nature 341:343–345 (1989).

Suzuki, et al., "Common Protein–binding Sites in the 5'–Flanking Regions of Human Genes for Cytochrome c1 and Ubiquitine–binding Protein," J. Biol. Chem. 265:8159–8163 (1990).

Temin, "Structure, variations and synthesis of retrovirus long terminal repeat," Cell 27:1–3 (1981).

Ting, et al., "Endogenous retroviral sequences are required for tissue–specific expression of a human salivary amylase gene," Genes & Dev. 6:1457–1465 (1992).

Tolstoshev, "Gene therapy, concepts, current trials and future directions, Ann. Rev. Pharm, Toicol. 32:573–596 (1993).

Tuan, et al., "Transcription of the hypersensitive site HS 2 enhancer in erythroid cells," *Proc. Natl. Acad. Sci USA* 89:11219–11223 (1992).

Tuan, et al., "An erythroid–specific, developmental–stage–independent enhancer far upstream of the human β–like globin genes," *Proc. Natl. Acad. Sci. USA* 86:2554–2558 (1989).

Tuan, et al., "The β–globin gene domain in human erythroid cells," *Proc. Natl. Acad. Sci USA* 82:6384–6388.

Yang, et al., "The nucleotide sequence of a new human repetitive DNA consists of eight tandem repeats of 66 base pairs," *Gene* 25:59–66 (1983).

Yu, et al., "A 5' β–globin matrix–attachment region and the polyoma enhancer together confer position–independent transcription," *Gene* 139:139–145 (1994).

Weber–Benarous, et al., "Retroviral–mediated transfer and expression of human β–globin genes in cultured murine and human erythroid cells," J. Biol. Chem. 263:6142–6145 (1988).

Weinberg, et al., "Productive human immunodeficiency virus type 1 (HIV–1) infection of nonproliferating human monocytes." J. Exp. Med. 174(6):1477–82 (1991).

Wickrema, et al., "Differentiation and erythroid expression in human erythroid progenitor cells," Blood 50:1940–45 (1992).

Zucchi & Schlessinger "Distribution of moderately repetitive sequences pTR5 and LF1 in Xq24–q–28 human DNA and their use in assembling YAC contigs, " Genomics 12:264–275 (1992).

Ludwig, et al., "Ku80 gene expression is Sp1–dependent and sensitive to CpG methylation within a novel cis element, "Gene 199;181–194 (1997).

Merika & Orkin, "DNA–binding specificity of GATA family transcription factors," Mol. Cell. Biol. 13:3999–4010 (1993).

Miller, "Retroviral vectors," Curr. Top. Microbiol. Immunol. 158:1–24 (1992).

Miller & Bieker, "A novel, erythroid cell–specific murine transcription factor that binds to the CACCC element and is related to the Kruppel family of nuclear proteins," Mol. Cell. Biol. 13:1776–2786 (1993).

Miller, "Human gene therapy comes of age," Nature 357(6378): 455–60 (1992).

Morgan & Anderson, "Human gene therapy," Annu. Rev. Biochem. 62:191–217 (1993).

Mulligan, "The basic science of gene therapy," Science 260(5110):926–32 (1993).

Nienhuis, et al.,"Advances in thalassemia research," Blood 63:738–758 (1984).

* cited by examiner

```
GTAAATACACCACTCGGCAGTCTGTATCTAGCTCAAGGTTTGTAAACACCAATCAGCA  1020
CCCTGTGTCTAGCTCAGGGTTTGTGAATGCACCAATCAACACTCGTATCTAGCTACTCT  1080
GGTGGGACTTGGAGAACCTTTGTGTGGACACTCTGTATCTAGCTAATCTGGTGGGACGT  1140
GGAGAACCTTTGTGTCTAGCTCATGGATTGTAAATGCACCAATCAGTGCCCTGTCAAAAC  1200
AGACCACTGGGCTCTCTACCAATCAGCAGGATGTGGGCCAGATAAGAGAATAAAA  1260
GCAGGCTGCCCGAGCCAGCAGTGGCAACCCGCTCGGGTCCCCTTCCACACTGTGGAAGCT  1320
TTGTTCTTTCGCTCTTTGCAATAAACTTGCTGCTCACTGTTTGGGTCTACACTGCC  1380
TTTATGAGCTGTAACGCTCACCGGAAGCTCTGCAGCTTCACTCTTGAAGCCAGCGAGAC  1440
CACGAACCCACCGGAGAACGAACAACTCCAGAGGGCCGCTTAAGAGCTGGAACGTTCA  1500
CTGTGAAGGTCTGCAGCTTCACTCCTGAGCCAGCGAACCCATCAGAAGGAAG  1560
AACTCGAACACATCCAAACATCCAGAACGAACAACTCCACACACGCGAGCCTTTAAGAACTG  1620
TAACACTCACCAGAGGGTCCCCGGCTTCATTCTTGAAGTCAGTGAAACCAAGAACCCAC  1680
CAATTCCGGACACAGTATGTCAGAAACAATATGAGTCACTAAATCAATATACTTCTCAAC  1740
AACAGCCCTTGCAATTAACTTGGCCATGTGACTGGTTGTGACTAAAATAATGTGGAGATA  1800
ATAATGTGTTACTCCCTAAGGCAGAGTGCCC
```

| | | |
|---|---|---|
| 1 | LTR \| CAT | LTR-CAT |
| 2 | Ups \| CAT | Ups-CAT |
| 3 | εp \| CAT | εp-CAT |
| 4 | HS2 \| εp \| CAT | HS2-εp-CAT |
| 5 | LTR \| εp \| CAT | LTR-εp-CAT |
| 6 | HS5 \| εp \| CAT | HS5-εp-CAT |
| 7 | LTR \| HS5 \| εp \| CAT | LTR-HS5-εp-CAT |

Figure 7

1. To replace the LTRs or their component U3, R and U5 regions of retroviral vectors designed for gene therapy of hereditary or acquired hematological diseases.

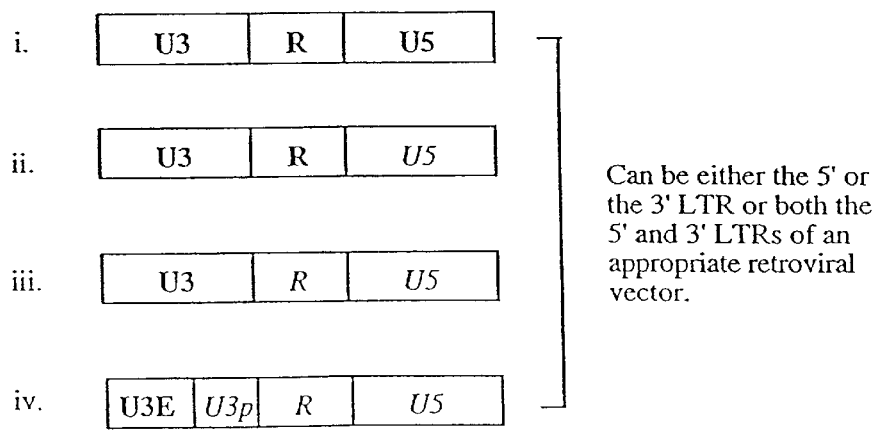

U3: the U3 enhancer and promoter of the 5'HS5 ERV-9 LTR
R: the R region of the 5'HS5 ERV-9 LTR
U5: the U5 region of the 5'HS5 ERV-9 LTR
U3E: the U3 enhancer of the 5'HS5 ERV-9 LTR
*U3p, R and U5*: the U3 promoter, R and U5 regions of appropriate non-5'HS5 ERV-9 LTRs.

*Figure 11*

2. To activate in hematopoietic cells the transcription of a cis-linked transgene spliced in either viral or non-viral vectors.

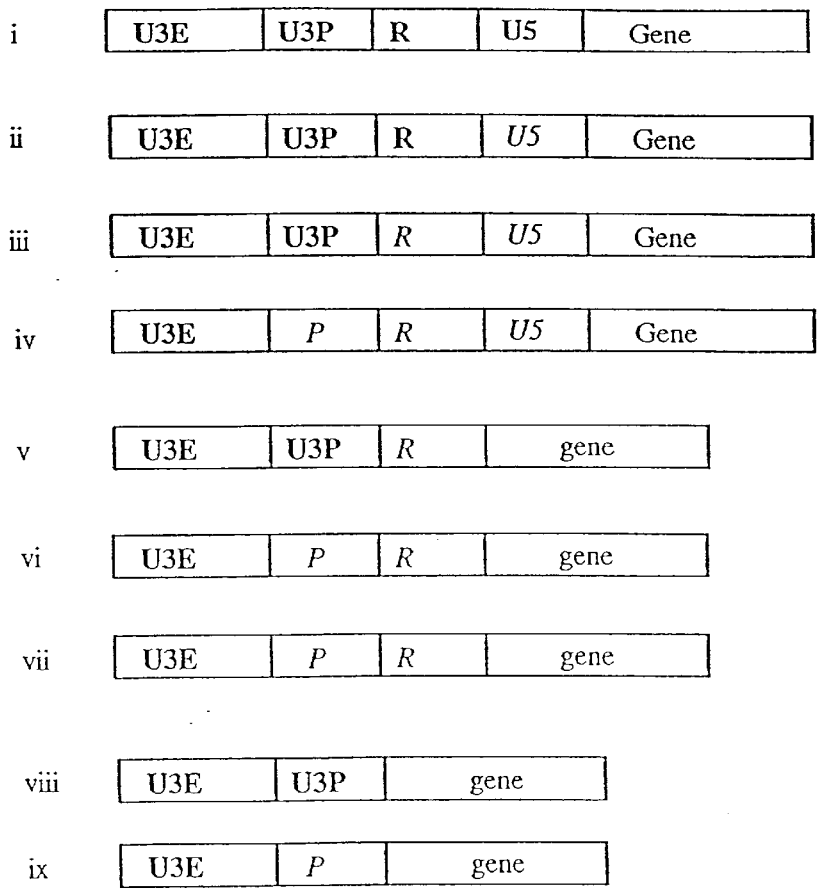

U3: the U3 enhancer and promoter of the 5'HS5 ERV-9 LTR
R: the R region of the 5'HS5 ERV-9 LTR
U5: the U5 region of the 5'HS5 ERV-9 LTR
U3E: the U3 enhancer of the 5'HS5 ERV-9 LTR
U3P: the U3 promoter of the 5'HS5 ERV-9 LTR R and U5: the R and U5 regions of appropriate non-5'HS5 ERV-9 LTRs.
P: appropriate promoter other than the U3 promoter of the 5'HS5 ERV-9 LTR.

Figure 12

Design of the vectors:

Can be either the 5' or the 3' LTR or both the 5' and 3' LTRs of an appropriate retroviral vector.

Hatched box: the U3 insulator sequence.
E and P: appropriate enhancer and promoter sequences.
gene: appropriate transgene
all other designations: the same as Figure 12

LONG TERMINAL REPEAT, ENHANCER, AND INSULATOR SEQUENCES FOR USE IN RECOMBINANT VECTORS

CROSS-REFERENCE TO RELATED APPLICATIONS

This application claims benefit of U.S. Provisional Application No. 60/105,256, filed Oct. 22, 1998. Application Ser. No. 60/105,256, filed Oct. 22, 1998, is hereby incorporated herein by reference.

BACKGROUND OF THE INVENTION

The human endogenous retroviruses (HERVs) were inserted into the germ cells of primates millions of years ago and have remained as an integral part of the primate genomes during evolution. In addition to the proviruses, solo LTRs are also dispersed throughout the human genome (Wilkinson et al, 1994; Lower et al, 1996). The solo LTRs contain the U3, R and U5 regions (Temin, 1982) but no internal gag, pol and env genes. Together, the HERVs and the solo LTRs comprise approximately 5% of the human genome and belong to the category of middle repetitive DNAs characterized as retrotransposons (A.F. Smit, 1996; Henikoff et al, 1997).

The ERV-9 proviruses, containing 30–50 members, constitute one of many families of the HERVs (Wilkinson et al, 1994; Lower et al, 1996). In addition to the proviruses, solo ERV-9 LTRs with a copy number of 3000–4000 have been found in the human genome (Henthorn et al, 1986; La Mantia et al, 1991; Zucchi and Schlessinger, 1992). The ERV-9 retrotransposons were inserted into the primate genome probably as early as ten million years ago (Di Cristofano et al, 1995). The retrotransposons have been suggested to be selfish DNAs irrelevant to the cellular functions of the hosts (Doolittle and Sapienza, 1980). However, recent findings indicate that the enhancer and promoter elements in the U3 region of the LTRs (Lenz et al, 1984; Speck et al, 1990) initiate and promote the transcription of host genes located immediately downstream of the LTRs and may thus serve relevant cellular functions (Stavenhagen and Robins, 1988; Feuchter et al, 1992; Goodchild et al, 1992; Ting et al, 1992; Schulte et al, 1996).

The human β-like globin genes consist of the embryonic ε the fetal Gγ and Aγ, and the adult δ and β genes located on Chromosome 11 in a transcriptional order of 5' ε-Gγ-Aγ-δ-β 3' (Efstratiadis et al, 1980). The transcription of these genes is regulated by the far upstream Locus Control Region (LCR), which is defined by four erythroid specific, DNase I hypersensitive sites HS 1, 2, 3 and 4 (Tuan et al, 1985; Forrester et al, 1987; Grosveld et al, 1987; Dhar et al, 1990). The LCR between HS1 and HS4 is present in other mammals from mouse to galago and comprises the major functional component of the LCR (reviewed by Hardison et al, 1997). A ubiquitous HS5 site has been identified further upstream of the HS 1–4 sites (Tuan et al, 1985; Dhar et al, 1990) in the apparent 5' boundary area of the LCR.

Enhancer elements are cis-acting and increase the level of transcription of an adjacent gene from its promoter in a fashion that is relatively independent of the position and orientation of the enhancer element. In fact, Khoury and Gruss, 1983, Cell 33:313, state that "the remarkable ability of enhancer sequences to function upstream from, within, or downstream from eukaryotic genes distinguishes them from classical promoter elements . . . " and suggest that certain experimental results indicate that "enhancers can act over considerable distances (perhaps >10 kb)."

Enhancer elements have been identified in a number of viruses, including polyoma virus, papilloma virus, adenovirus, retrovirus, hepatitis virus, cytomegalovirus, herpes virus, papovaviruses, such as simian virus 40 (SV40) and BK, and in many non-viral genes, such as within mouse immunoglobulin gene introns. Enhancer elements may also be present in a wide variety of other organisms. Host cells often react differently to different enhancer elements. This cellular specificity indicates that host gene products interact with the enhancer element during gene expression.

Although gene replacement by homologous recombination could be used instead of integrating vectors, this approach is not yet technically practical because of the very low success rate of the homologous recombination events and the inability to culture the pluripotent stem cells required for this approach.

BRIEF SUMMARY OF THE INVENTION

Disclosed are an enhancer, insulator, and promoter from the HS5 region in the 5' boundary area of the locus control region of human β-like globin genes. These transcription control sequences can be used to control expression of any desired gene of interest and can be used in any vector for this purpose. The control sequences are derived from the area in and around the U3 region of a solitary endogenous retrovirus (ERV) 9 long terminal repeat (LTR).

Also disclosed are methods of expressing any gene of interest. For this purpose, the control sequences can be operably linked to the gene of interest (and operably linked to each other). The disclosed enhancers, insulators, and promoters can also be used with any other control sequences. Preferably, the control sequences are used in vectors to obtain expression of a gene of interest in a cell, including cells in animals.

BRIEF DESCRIPTION OF THE DRAWINGS

FIGS. 2A and 2B is the sequence of the 5'HS5 LTR in the 5'ε1.4 phage DNA clone from K562 cells (SEQ ID NO:1). The four bases GTAT with the heavy overline and underline located at the 5' and 3' ends of the LTR are the presumed integration site of the LTR in the human genomic DNA. The horizontal arrows in U3 are the 14 tandem repeats of 37–41 bases in the U3 region. Angled arrow is the presumed transcriptional initiation site in the LTR, marking the beginning of the R region. The long horizontal arrows in the U5 region are the three repeats of 70 bases in U5. Arrowheads connected to dotted overlines are locations of the PCR primers used in DNA PCR and RT-PCR studies discussed in Example 1. Directions of the arrowheads are the 5' to 3' direction of the primers.

FIGS. 5A–5D is a sequence alignment of the normal human (Hu N; of SEQ ID NO:25), truncated human (Hu S; SEQ ID NO:6) and gorilla (Gori; SEQ ID NO:7) LTRs. Majority bases represents the consensus DNA sequence among the three LTRs (SEQ ID NO:5). Numbers between two horizontal lines are the DNA base ruler with base 1 being the first base of the first U3 repeat in the LTRs. Vertical arrows are the positions of the first base in the U3 repeats. Dots represent the same bases in the human or gorilla DNAs as those in the consensus sequence. Dashes represent base deletions. The GTAT bases at positions 1081–84 marked with heavy overline are the integration site of the 5'HS5 LTR in both human and gorilla DNAs.

FIG. 7 is a diagram of the structure of recombinant CAT constructs. LTR is a 1 kb LTR sequence. Ups is 1.2 kb of DNA upstream of the LTR (see FIG. 1). εp is a 200 bp ε-globin promoter. HS2 is a 0.74 kb HS2 enhancer. HS5 is a 1.2 kb sequence spanning the HS5 site.

FIG. 11 is a diagram of examples of constructs using the disclosed enhancers and promoters.

FIG. 12 is a diagram of examples of constructs using the disclosed enhancers and promoters.

DETAILED DESCRIPTION OF THE INVENTION

Transcription of the human β-like globin genes in erythroid cells is regulated by the far-upstream locus control region (LCR). Five kilobases of new upstream DNA were cloned and sequenced in order to define the 5' border of the LCR. An LTR-retrotransposon belonging to the ERV-9 family of human endogenous retroviruses was found in the apparent 5' boundary area of the LCR. This ERV-9 LTR contains an unusual U3 enhancer region comprised of fourteen tandem repeats with recurrent GATA, CACCC and CCAAT motifs. This LTR is conserved in human and gorilla, indicating its evolutionary stability in the genomes of primates. In both recombinant constructs and the endogenous human genome, the LTR enhancer and promoter activate the transcription of cis-linked DNA preferentially in erythroid cells.

Figure 1:
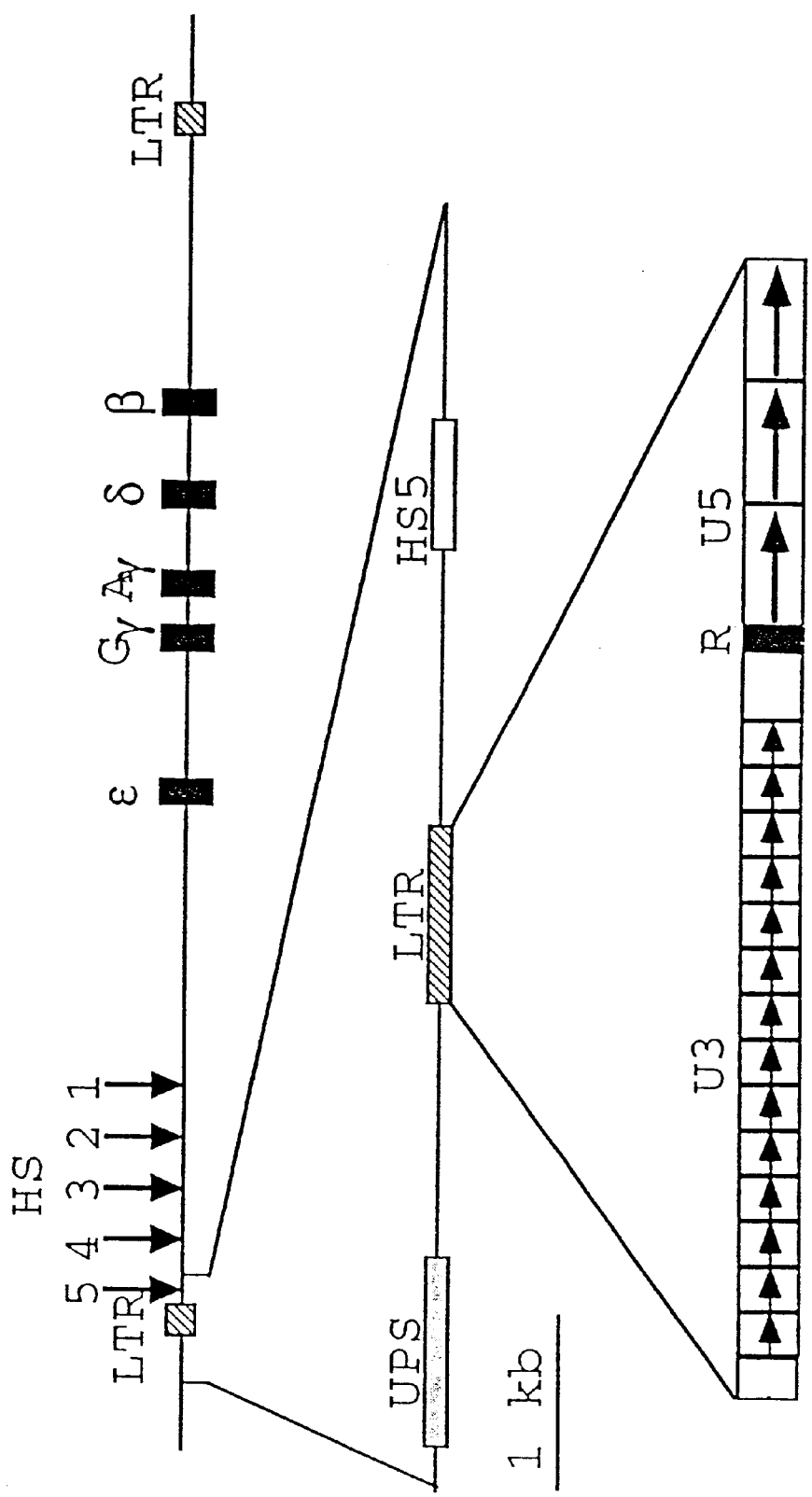
FIG. 1 is a diagram of the location and structure of the ERV LTR in the boundary area of the β-globin LCR. The top line shows the human β-like globin gene locus. Solid Boxes are the embryonic ε-, fetal γ- and adult δ- and β-globin genes. The vertical arrows indicate locations of the DNase I hypersensitive sites HS 1, 2, 3, 4 and 5. The hatched box 5' of the HS5 site is a solo ERV-9 LTR. The hatched box 3' of the β-globin gene is a second copy of the ERV-9 LTR located 30 kb 3' of the β-globin gene (Henthorn et al, 1986; Anagnou et al, 1995). The middle line is the enlarged 5' boundary area drawn to scale according to the 1 kb scale bar. Open, hatched and gray boxes are respective locations of the HS5 site, ERV-9 LTR and an arbitrary upstream region (Ups) which was used as a control sequence for the LTR in reporter gene assays and RT-PCR studies. The bottom line is the structure of the LTR. Short horizontal arrows are the 14 short tandem repeats in the U3 region. Solid bar is the R region. Long horizontal arrows are the three longer repeats in the U5 region.

Sequencing data of the 5' border region of the LCR reveal a solitary ERV-9 LTR with the characteristics of a retrotransposon in a location near the HS5 site (see FIG. 1). This 5' HS5 LTR possesses an unusual sequence feature in the U3 enhancer region which is comprised of fourteen tandem repeats of a consensus DNA of 41 bases. These U3 repeats as well as the downstream promoter contain recurrent GATA, CACCC and CCAAT motifs. This LTR-retrotransposon is conserved with 98–99% sequence identities in people of different races and in the gorilla, except that some people have eleven instead of fourteen U3 repeats and the gorilla has only five U3 repeats. Functional tests with the CAT reporter gene assays demonstrate that the human 5' HS5 LTR activates the cis-linked CAT gene and possesses enhancer and promoter activities in erythroid cells. In the CAT reporter gene assays, the LTR also synergized with and activated the cis-linked HS5 site. Consistent with these results, RT-PCR studies of cellular RNAs isolated from human primary cells and cell lines indicate that the endogenous LTR activates transcription of the downstream R, U5 and the genomic DNA at a higher level in erythroid than in nonerythroid cells.

Disclosed are enhancers, insulators, and promoters derived from the HS5 region in the 5' boundary area of the locus control region of β-like globin genes. These transcription control sequences can be used to control expression of any desired gene of interest and can be used in any vector for this purpose. The control sequences are derived from the area in and around the U3 region of a solitary endogenous retrovirus long terminal repeat (ERV-9 LTR).

Also disclosed are methods of expressing any gene of interest. For this purpose, the control sequences can be operably linked to the gene of interest (and operably linked to each other). The disclosed enhancers, insulators, and promoters can also be used with any other control sequences. Preferably, the control sequences are used in vectors to obtain expression of a gene of interest in a cell, including cells in animals.

Current strategies for gene expression in mammals and mammalian cells, especially gene therapy of hereditary or acquired blood diseases, employ retrovirus-mediated gene-transfer techniques. One of the common problems of this approach has been the extinction of the expression of the transgenes by the long terminal repeats (LTRs) of the vector flanking the therapeutic transgene and by the host sequences flanking the LTR-transgenic cassette. The disclosed enhancers—derived from the powerful enhancer discovered in the solitary LTR of the ERV-9 human endogenous retrovirus located in the 5' border of the β-globin Locus Control Region—can alleviate this problem. The ERV-9 LTR-enhancer is most active in erythroid cells and can thus be used to replace the LTR in the retroviral vector to avoid the transcriptional silencing of the transgene and to boost the transcription of the therapeutic transgene in erythroid progenitor cells. Another problem with gene expression in animal and mammalian cells, interference from flanking transcription, can be alleviated using the disclosed insulator. The disclosed insulators are derived from a stretch of LTR DNA of 600 bases, which contains a very high G and C bases of 70% and is located immediately upstream of the ERV-9 LTR enhancer. The disclosed insulators can be used to insulate expression cassettes, especially those to be inserted in the genome of the host cell, from the transcriptional interference and silencing of the flanking host sequences.

The solitary ERV-9 LTR sequence in the β-globin Locus Control Region belongs to middle repetitive sequences in the human genome with a haploid copy number of 3000–4000. The first copy of a solitary ERV-9 LTR was reported in 1989. The functional significance of the ERV-9 LTRs dispersed in the human genome may be to transcriptionally activate and thus mark the cis-linked loci of hematopoietic genes and gene families in early progenitor cells during ontogeny and hematopoietic lineage differentiation and the specific function of the solo ERV-9 LTR located near the HS5 site in the 5' border of the human β-globin locus control region (LCR) may initiate transcription of the LCR during early stages of ontogeny and this transcription process of the LCR regulates the transcriptional activation of the further downstream β-like globin genes during erythropoiesis.

Specifically disclosed are nucleic acid molecules comprising all or a functional portion of the U3 enhancer (nucleotides 595 to 1193 of FIG. 2; nucleotides 595 to 1193 of SEQ ID NO:1), or modified forms of the U3 enhancer, where a functional portion is a portion of the U3 enhancer that retains enhancer function. Also disclosed are nucleic acid molecule comprising all or a functional portion of the U3 insulator (nucleotides 5 to 594 of FIG. 2; nucleotides 5 to 594 of SEQ ID NO:1), or modified forms of the U3 insulator, where a functional portion of the U3 insulator is a portion of the U3 insulator that retains insulator function. Also disclosed are nucleic acid molecules comprising (1) all or a functional portion of the U3 enhancer (nucleotides 595 to 1193 of FIG. 2; nucleotides 595 to 1193 of SEQ ID NO:1), or modified forms of the U3 enhancer, operably linked to (2) all or a functional portion of the U3 insulator (nucleotides 5 to 594 of FIG. 2; nucleotides 5 to 594 of SEQ ID NO:1), or modified forms of the U3 insulator, where a functional portion is a portion of the U3 enhancer that retains enhancer function and where a functional portion of the U3 insulator is a portion of the U3 insulator that retains insulator function.

Also disclosed are nucleic acid molecules comprising all or a functional portion of the U3 promoter (nucleotides 1194 to 1322 of FIG. 2; nucleotides 1194 to 1322 of SEQ ID NO:1), or modified forms of the U3 promoter, where a functional portion of the U3 promoter is a portion of the U3 promoter that retains promoter function. Also disclosed are nucleic acid molecules comprising (1) all or a functional portion of the U3 enhancer (nucleotides 595 to 1193 of FIG. 2; nucleotides 595 to 1193 of SEQ ID NO:1), or modified forms of the U3 enhancer, operably linked to (2) all or a functional portion of the U3 promoter (nucleotides 1194 to 1322 of FIG. 2; nucleotides 1194 to 1322 of SEQ ID NO: 1), or modified forms of the U3 promoter, where a functional portion is a portion of the U3 enhancer that retains enhancer function and where a functional portion of the U3 promoter is a portion of the U3 promoter that retains promoter function.

Also disclosed are nucleic acid molecules comprising the U3 R region (nucleotides 1322 to 1380 of FIG. 2; nucleotides 1322 to 1380 of SEQ ID NO:1), or modified forms of the U3 R region. Also disclosed are nucleic acid molecules comprising (1) all or a functional portion of the U3 enhancer (nucleotides 595 to 1193 of FIG. 2; nucleotides 595 to 1193 of SEQ ID NO:1), or modified forms of the U3 enhancer, operably linked to (2) the U3 R region (nucleotides 1322 to 1380 of FIG. 2; nucleotides 1322 to 1380 of SEQ ID NO:1), or modified forms of the U3 R region, where a functional portion is a portion of the U3 enhancer that retains enhancer function.

Also disclosed are nucleic acid molecules comprising (1) all or a functional portion of the U3 enhancer (nucleotides 595 to 1193 of FIG. 2; nucleotides 595 to 1193 of SEQ ID NO:1), or modified forms of the U3 enhancer; operably linked to (2) all or a functional portion of the U3 insulator (nucleotides 5 to 594 of FIG. 2; nucleotides 5 to 594 of SEQ ID NO:1), or modified forms of the U3 insulator; and operably linked to (3) all or a functional portion of the U3 enhancer (nucleotides 595 to 1193 of FIG. 2; nucleotides 595 to 1193 of SEQ ID NO:1), or modified forms of the U3 enhancer; where a functional portion is a portion of the U3 enhancer that retains enhancer function, where a functional portion of the U3 insulator is a portion of the U3 insulator that retains insulator function, and where a functional portion of the U3 promoter is a portion of the U3 promoter that retains promoter function.

Enhancers

The disclosed enhancers have enhancer function. Enhancers function to increase the transcription from promoters in proximity to the enhancer. The disclosed enhancers, like many enhancers, can function both upstream and downstream from a gene, and in either orientation. The disclosed enhancers are, or are derived from, all or a functional portion of the U3 enhancer (nucleotides 595 to 1193 of FIG. 2; nucleotides 595 to 1193 of SEQ ID NO:1), or modified forms of the U3 enhancer, where a functional portion is a portion of the U3 enhancer that retains enhancer function. The disclosed enhancers can be combined with other transcription control elements, including the disclosed insulators and promoters.

Disclosed are primate 5' HS5 ERV-9 LTR enhancers. In particular, human and gorilla 5' HS5 ERV-9 LTR enhancers are disclosed. A preferred form of enhancer is the U3 enhancer present on nucleotides 595 to 1193 of FIG. 2 (nucleotides 595 to 1193 of SEQ ID NO:1). The U3 enhancer is made up of fourteen repeat units, where each repeat has one of the following four sequences:
TATCTAGCTCAGGGATTGTAAATACAC-CAATCGGCAGTCTG (SEQ ID NO:8),
TGTCTAGCTCAAGGTTTGTAAACACAC-CAATCAGCACCCTG (SEQ ID NO:9),
TATCTAGCTCAGGGTTTGTGAATGCAC-CAATCAACACTCTG (SEQ ID NO:10),
TGTCTAGCTACTCTGTGGGGACGTG-GAGAACCTTTA (SEQ ID NO:11).

Also disclosed are modified forms of the U3 enhancer where the modified enhancer retains enhancer function. These include:

Enhancers having three or more repeats, where each repeat has one of the following sequences:
TRTCTAGCTCADGGTTTGTRAAYRCAC-CAATCAGCACTCTG (SEQ ID NO:12),
TATCTAGCTCAGGGATTGTAAATACAC-CAATCGGCAGTCTG (SEQ ID NO:8),
TGTCTAGCTCAAGGTTTGTAAACACAC-CAATCAGCACCCTG (SEQ ID NO:9),
TATCTAGCTCAGGGTTTGTGAATGCAC-CAATCAACACTCTG (SEQ ID NO:10),
TGTCTAGCTACTCTGTGGGGACGTG-GAGAACCTTTA (SEQ ID NO:11).

Enhancers having three or more repeats, where each repeat has one of the following sequences:
TATCTAGCTCAGGGATTGTAAATACAC-CAATCGGCAGTCTG (SEQ ID NO:8),
TGTCTAGCTCAAGGTTTGTAAACACAC-CAATCAGCACCCTG (SEQ ID NO:9),
TATCTAGCTCAGGGTTTGTGAATGCAC-CAATCAACACTCTG (SEQ ID NO:10),
TGTCTAGCTACTCTGTGGGGACGTG-GAGAACCTTTA (SEQ ID NO:11).

Enhancers having three or more repeats, where each repeat has the following sequence:
TRTCTAGCTCADGGTTTGTRAAYRCAC-CAATCAGCACTCTG (SEQ ID NO:12).

Enhancers where the enhancer has from three to fourteen repeat units.

Enhancers where one or more of the repeat units of the enhancer are deleted, one or more of the repeat units are replaced with a repeat unit of the enhancer having a different sequence than the repeat unit that is replaced, one or more repeat units of the enhancer are added to the enhancer, or a combination of one or more of these modifications.

The disclosed control sequences can be used, alone or in combination, to express any gene of interest. For this purpose, the control sequences can be operably linked to the gene of interest. Preferably, the gene encodes a protein. Preferably, the control sequences are used in vectors to obtain expression of a gene of interest in a cell, including cells in animals. Preferred vectors include retroviral vectors, adenoviral vectors, and other vectors suitable for gene expression in mammalian cells and/or suitable for gene therapy. Many vectors are known and the disclosed control sequences can be used in any of these vectors.

Also disclosed are cells transformed with vectors containing one or more of the disclosed control sequences. That is vectors containing one or more of the disclosed enhancers, insulators, or promoters. Preferred cells are eukaryotic cells, animal cells, and mammalian cells. Also disclosed is a method of expressing a protein, the method comprising culturing cells transformed with a vector containing one or more of the disclosed control sequences operably linked to the gene. Also disclosed is a method of expressing a gene in an animal, the method comprising introducing into the animal cells transformed with a vector containing one or more of the disclosed control sequences operably linked to the gene. Also disclosed is a method of expressing a gene in an animal, the method comprising introducing into cells of an animal a vector containing one or more of the disclosed control sequences operably linked to the gene.

Insulators

Insulators are nucleic acid segments that reduce or eliminate transcription from adjacent regions from affecting the nucleic acid segment to which the insulator is associated. The disclosed insulators preferably are placed upstream of other control sequences and/or downstream of genes. Insulators are preferably placed between different genes, transcription units, or genetic domains to reduce or prevent interference of the adjacent expression sequences. The disclosed insulators are, or are derived from, all or a functional portion of the U3 insulator (nucleotides 5 to 594 of FIG. 2; nucleotides 5 to 594 of SEQ ID NO:1), or modified forms of the U3 insulator, where a functional portion of the U3 insulator is a portion of the U3 insulator that retains insulator function.

Promoters

Promoters are nucleic acid segments that mediate initiation of transcription. The disclosed promoters are, or are derived from, all or a functional portion of the U3 promoter (nucleotides 1194 to 1322 of FIG. 2; nucleotides 1194 to 1322 of SEQ ID NO:1), or modified forms of the U3 promoter, where a functional portion of the U3 promoter is a portion of the U3 promoter that retains promoter function.

Use Of Control Elements

The disclosed enhancers, insulators, and promoters can be used in a variety of vectors and expression constructs to regulate and promote transcription of genetic elements placed in the same constructs. The disclosed control elements are preferably used in retroviral vectors to obtain expression in mammalian cells, and especially to express genes in cells in, or to be introduced into, animals (including humans) for gene therapy.

Specific examples of such uses are:

1. The 5'HS5 ERV-9 LTR and/or its component U3 enhancer, insulator, and promoter, the R and the U5 regions can be used to replace the LTRs or their equivalent U3, R and U5 regions of retroviral vectors designed for gene therapy of hereditary or acquired hematological diseases including sickle cell disease, thalassemias, leukemias and AIDS.
2. The U3 enhancer, insulator, and promoter, and the R region can be used to activate (and/or insulate) in hematopoietic cells the transcription of a cis-linked transgene in either viral or non-viral vectors. The host cells for the transgene can be the hematopoietic stem cells, progenitor cells or mature lineage differentiated cells such as the erythroid, myeloid or lymphoid cells.
3. Base mutations, and/or rearrangements and substitution of repeat units, can be introduced into the U3 and R regions to enable the U3 enhancer and promoter and the R region to work more efficiently in a specific hematopoietic lineage such as the erythroid, myeloid or lymphoid lineage.

Figure 13:
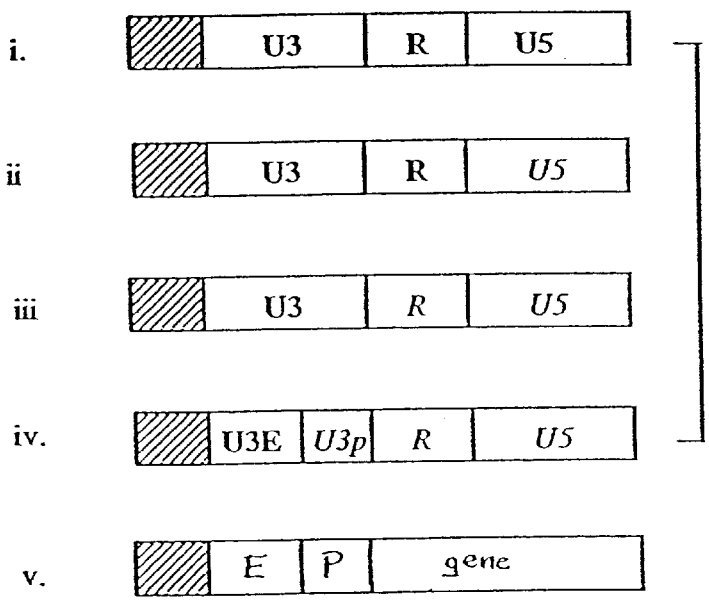
FIG. 13 is a diagram of examples of constructs using the disclosed insulators.

Design of the retroviral vectors and transgenic cassettes.
1. The disclosed enhancers, promoters, R region, and U5 region can be used to replace the LTRs or their component U3, R and U5 regions of retroviral vectors designed for gene therapy of hereditary or acquired hematological diseases. The disclosed insulators can also be added to the vector. The replacement can be in either the 5' or the 3' LTR or both the 5' and 3' LTRs of an appropriate retroviral vector. Example constructs are shown in FIG. 11.
U3: the U3 enhancer and promoter of the 5'HS5 ERV-9 LTR
R: the R region of the 5'HS5 ERV-9 LTR
U5: the U5 region of the 5'HS5 ERV-9 LTR
U3E: the U3 enhancer of the 5'HS5 ERV-9 LTR
U3p, R and U5: the U3 promoter, R and U5 regions of appropriate non-5'HS5 ERV-9 LTRs.
2. Constructs such as those shown in FIG. 12 can be used to activate the transcription of cis-linked transgene spliced in either viral or non-viral vectors in hematopoietic cells.
U3: the U3 enhancer and promoter of the 5'HS5 ERV-9 LTR
R: the R region of the 5'HS5 ERV-9 LTR
U5: the U5 region of the 5'HS5 ERV-9 LTR
U3E: the U3 enhancer of the 5'HS5 ERV-9 LTR
U3P: the U3 promoter of the 5'HS5 ERV-9 LTR
R and U5: the R and U5 regions of appropriate non-5'HS5 ERV-9 LTRs.
P: appropriate promoter other than the U3 promoter of the 5'HS5 ERV-9 LTR.
3. The disclosed insulators can be used to insulate integrated transgenes in hematopoietic and non-hematopoietic cells from transcriptional interference exerted by the host genome and or elimination by the host genome over time, so that the transgene can be efficiently transcribed from its own enhancer and promoter and also can be stably integrated in the host genome over time. Examples of constructs using the disclosed insulators are shown in FIG. 13. Such constructs will have improved expression consistency and stability by limiting or eliminating the influence of flanking transcription activities.

The U3 enhancer repeats of the 5'HSS LTR can also be used to identify transcription factors that bind to the enhancer. The transcription factors bound by the DNA motifs in U3 repeats can be identified by electrophoretic mobility shift assays (EMSA) with nuclear extracts isolated from cells, such as K562 and placenta trophoblasts, and supershift assays with antibodies against various known transcription factors. Such techniques for use with other protein binding sites are well established and can be used with the disclosed enhancers.

The genes encoding new transcription factors identified through this process can then be cloned. The molecular architecture and activity of the U3 enhancer complex can also be examined by site-directed mutagenesis of the U3 repeats in test plasmids containing the Green Fluorescent Protein (GFP) reporter gene, following transfection into cells, such as K562, CFU-E and placental trophoblast cells.

Constructs and Vectors

The disclosed control elements (that is, the disclosed enhancers, insulators, and promoters) are useful for expression of any desired gene. For this purpose, the disclosed control elements can be included in constructs and vectors designed for expression of genes of interest. Many such vectors are known. Preferred vectors are those for use in animals cells, and in particular, those for use in mammalian cells.

Examples of vectors and delivery techniques that can be adapted for use with the disclosed control elements are described in U.S. Pat. Nos. 5,968,735, 5,965,440, 5,965,358, 5,932,210, 5,925,565, 5,888,820, 5,888,767, 5,886,166, 5,871,997, 5,866,696, 5,866,411, 5,858,744, 5,856,152, 5,837,503, 5,830,727, 5,817,492, 5,814,482, 5,811,260, 5,795,577, 5,789,244, 5,783,442, 5,770,400, 5,759,852, 5,756,264, 5,753,499, 5,744,133, and 5,710,037.

Gene Therapy

The disclosed control elements can be used in vectors and constructs for gene therapy. "Gene therapy" refers to the treatment of pathologic conditions by the addition of exogenous nucleic acids to appropriate cells within the organism. The disclosed control elements can be used to express and increase the efficiency of expression of genes added in gene therapy. Nucleic acids must be added to the cell, transfected or transfected, such that they remain functional within the cell. The disclosed insulators can protect introduced genes from interfering endogenous transcription at the site of insertion. For most gene therapy strategies, the new nucleic acids are designed to function as new genes, i.e., code for new RNA or messenger RNA, which in turn codes for new protein. Alternatively, therapeutic genes can produce antisense or ribozymes which can directly effect cellular or pathogen functions without having to express protein from MRNA. Gene therapy can be directed towards monogenetic disorders like adenosine deaminase deficiency and cystic fibrosis or to polygenetic somatic disorders like cancer.

Human gene therapy has been successfully applied to correct genetic diseases in adenosine deaminase deficiency (severe combined immunodeficiency) (Approved Protocol) "Treatment of Severe Combined Immunodeficiency Disease (SCID) Due to Adenosine Deaminase (ADA) Deficiency with Autologous Lymphocytes Transduced with a Human ADA Gene" Hum. Gene Ther. 1:327–362 (1990); Anderson, W. F. "Human Gene Therapy" Science 256:808–813) and famnilial cholesterolaemia (Grossman, et al. Nature Genetics 6:335–341 (1994)). Many new gene therapy protocols are in progress or being planned (Morgan and Anderson Ann. Rev. Biochem. 62:191–217 (1993)). Vectors, constructs, and protocols described in the studies above can be adapted for use with the disclosed control elements.

The rapid implementation of gene therapy in human trials has been made possible by the development of relatively efficient means of transferring new nucleic acids into cells, a process generally referred to as "gene transduction". The clinically applicable gene transduction methods fall into one of three categories: a) cationic lipids, (b) molecular conjugates and (c) recombinant viruses. These different means of accomplishing gene transfection have been recently reviewed by Morgan, Ann. Rev. Biochem. 62:191 (1992); Mulligan Science 260:926 (1993); and Tolstoshev Ann. Rev. Pharm. Toxicol. 32:573 (1993)). Any of these transfer systems can be used for constructs using the disclosed control elements.

Most of the successful human gene therapy protocols utilize vectors derived from defective murine leukemia retroviruses (Anderson Science 256:808–813 (1992); Miller Nature 357:455–460 (1992); Miller Curr. Top. Microbiol. Immunol. 158:1–24 (1992), for review of these vectors and the packaging cell lines, Miller, Methods in Enzymology 217:581–599 (1993)). Although there is a limitation in the size of the gene (up to 7 to 8 kb) that can be transducted, the retrovirus based vectors have the advantage in that they can incorporate a permanent copy of the delivered gene into the chromosomes of the recipient cells and therefore potentially can represent a cure for a disorder arising due to the expression of an undesirable protein, activation of an oncogene, or insufficient expression or expression of a defective protein. Due to their retroviral origins, the disclosed control elements are particularly suited for use in retroviral vectors.

The majority of the gene transfer procedures used to date for human gene therapy is known as an ex vivo gene transfer. The recipient cells are removed from the patient and grown in a cell culture laboratory. Replication-incompetent, virus-like particles containing the therapeutic gene, which are produced from packaging cells, are used to transduce the recipient cells. The transduced recipient cells are then selected by growing in selection media, expanded and returned to the patient. The packaging cells are genetically engineered cell lines that, once a therapeutic gene is transferred into the cells, produce virus-like particles containing the therapeutic gene to be delivered into other cells.

Other gene transferring vehicles in which the disclosed control elements can be used are those based on human immunodeficiency virus (HIV) (Poznansky, et al. J. Virol. 65:532–536 (1991); Buchschacher, et al. J. Virol. 66:2731–2739 (1992); Shimada, et al. J. Clin. Invest. 88:1043–1047 (1991)) and adeno-associated virus (Chatterjee, et al. Science 258:1485–1488 (1992); Muzyczka Curr. Top. Microbiol. Immunol. 158:97–129 (1992)).

An HIV based delivery system is believed to be particularly suitable for gene therapy against AIDS. Not only can the genes transferred by HIV virus-based vectors be integrated into the genome of non-dividing cells (Weinberg, et al. J. Exp. Med. 174:1477–1482 (1991); Bukrinsky, et al. Proc. Natl. Acad. Sci. U.S.A. 89:6580–6584 (1992); Lewis, et al. [published erratum appears in EMBO J. November 11(11):4249 (1992)] EMBO. J. 11:3053–3058 (1992)), the presence of HIV gp120 on the surface of the gene delivering particles renders them specific for gene delivery to CD4+ cells.

The U3 enhancer region in 5' HS5 LTR contains an unusual sequence of fourteen tandem repeats of 37–41 bases. The tandem repeats are comprised of four subtypes 1, 2, 3 and 4, which are arranged in the LTR in the order 1-2-3-4-1-2-3-4-1-2-3-4-4-1. The consensus sequence of the U3 repeats (SEQ ID NO:12) reveals five conserved motifs, GATA, TAGCTCA, GGTTTGT (or GGTGG/CCACC in subtype 4) and CCAAT. The motifs GATA, CCAAT and CACC can potentially bind to cognate transcription factors abundantly expressed in hematopoietic and erythroid cells.

Figure 3:
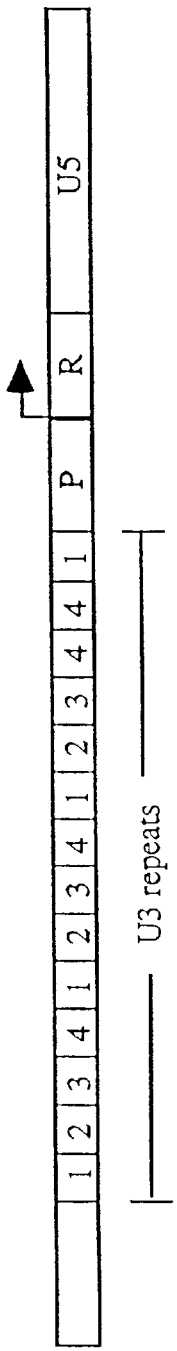
FIG. 3 is a comparison of the sequences of the U3 repeats. The top line is the organization of the four subtype U3 repeats 1, 2, 3 and 4 in 5'HS5 LTR. P is the promoter in the U3 region. In the middle are the sequences of the subtype repeats 1, 2, 3, and 4 (SEQ ID NOs:8, 9, 10, and 11, respectively). Underlined bases are the GATA, CCAAT, CACCC or CCACC motifs. At the bottom are consensus sequences of the U3 repeats in different ERV-9 LTRs. 5'HS5 (SEQ ID NO:12), 3'β (SEQ ID NO:13) and LTR2 (SEQ ID NO:14) are the 5'HS5 LTR, the LTR at 25 kb 3' of the β-globin gene (Henthorn et al, 1986; Anagnou et al, 1995), and the LTR in a random human DNA clone (Lania et al, 1992), respectively. Lower case letters separated by slashes indicate polymorphic bases in the U3 repeats.

The consensus sequence of U3 repeats shows higher than 90% sequence homology with that of the U3 repeats of the 3' εERV-9 LTR located 25 kb 3' of the β-globin gene and of LTR2, a random clone of ERV-9 LTR (FIG. 3).

The promoter sequence in the LTR is located in the U3 region at the 3' end of the U3 repeats and is immediately upstream of the transcribed R region whose 5' border marks the transcriptional initiation site for retroviral RNA synthesis. The promoter of the 5'HS5 LTR shows a sequence homology of 80% with the promoter of the 3' βLTR and of over 90% with the promoter of LTR2. The transcriptional initiation site of LTR2 has been determined by primer extension to be located 28 bases downstream of the AATAAAA box. Because of extensive sequence homologies between the 5'HS5 LTR and the LTR2 promoters, especially the 100% sequence homology in the 70 DNA bases flanking the AATAAAA box, the transcripitional initiation site of the 5'HS5 LTR was placed at the identical T base 28 bases downstream of the AATAAAA box. All three LTR promoters contain the GATA, CACCC and CCAAT motifs at identical locations, -36, -46 and -63 bases respectively, relative to the retroviral transcriptional initiation site.

The 5'HS5 LTR promoter also bears structural similarities with the promoters of the further downstream ε-, γ- and β-globin genes in that a combination of similar GATA, CACCC and CCAAT motifs is found also upstream of the AATAAAA boxes in the globin promoters. In particular, the 5'HS5 LTR and the ε-globin promoter share additional sequence homologies in the region immediately 5' of the transcriptional initiation site. The above homologies indicate that, like the globin promoters, the 5'HS5 LTR enhancer and promoter ought to be active in erythroid cells. Indeed, transfection assays show that the 5'HS5 LTR exhibits enhancer and promoter activities and can promote the transcription of cis-linked DNA to relatively high levels in erythroid cells and in placenta.

The consensus sequence of the modular U3 repeats in 5'HS5 LTR reveals that the modular U3 repeat contains five well conserved and recurrent DNA motifs organized invariably in the following 5'→3' order: GATA, TAGCTCA, GGTTTGT (or TGGTGGG in subtype 4) and CACCAAT-CAGCA (nucleotides 25 to 36 of SEQ ID NO:12). This invariable sequence structure suggests a definitive organization of the cognate protein factors in the assembly of the U3 enhancer complex.

The GATA motifs bind to the GATA family of transcription factors including GATA-1, -2 and -3. Targeted disruptions of the GATA-1, -2 and -3 genes have been reported to cause severe abnormaties in hematopoiesis and erythropoiesis, indicating that these factors play important regulatory roles in erythroid cells. Different GATA factors are expressed at relatively higher levels in different hematopoietic cells. In CD34+ hematopoietic stem/progenitor cells, GATA-2 is expressed at a high level relative to GATA-3 and GATA-1. In erythroid K562 cells, both GATA-1 and GATA-2 are expressed. In CFU-E, GATA-1 is the major detected GATA factor. In placenta trophoblasts, GATA-2 and GATA-3 are expressed.

The CACCC motifs bind to erytiroid transcription factors EKLF and BKLF. EKLF is expressed at very low levels in K562 cells expressing the embryonic globin program and at much higher levels in MEL cells expressing the adult globin program. Unlike EKLF, BKLF is expressed abundantly in embryonic yolk sac and fetal liver and is not confined to erythroid cells. However, the motif in the U3 repeats is CACC and not CACCC found in the strong EKLF and BKLF binding sites, and may thus bind to these factors weakly or bind to different factor(s).

The CCAAT motifs may bind to two families of protein factors, the C/EBPs expressed in various hematopoietic cells and adipocytes and the ubiquitous NF-Y complex. The C/EBP transcription factors include C/EBP α, β, γ, δ, ε, and CHOP, a dominant negative inhibitor of the C/EBPs. They bind to the CCAAT motifs as a homodimer or hetetodimer through the β-ZIP domain. The CCAAT boxes have been reported to play pivotal roles in the activities of the globin promoters, suggesting the existence in erythroid cells of transcription factors that bind to and activate the CCAAT boxes. However, none of the C/EBP α, β, δ, and ε are present at detectable levels in erythtoid K562 cells and C/EBP γ, a ubiquitous factor, appears to be expressed mainly in lymphoid cells. This suggests that in K562 cells the CCAAT box may be bound paradoxically by negative regulators CHOP and CDP or primarily by the ubiquitous NF-Y complex.

The NF-Y complex, also named CP1, consists of three subunits A, B and C. All three subunits are required for binding to the CCAAT box as a trimeric complex through the histone fold motif, which bears similarity to the DNA binding domain of the histones. The NF-Y factors through the histone fold domain may also associate with histone acetyltransferase and thus be able to remodel and open up the chromatin structure of the CCAAT box and its neighboring DNA. In EMSA gels with nuclear extract from erythroid cells, after the NF-Y complex was supershifted with antibodies, the CCAAT box containing probe still formed shifted complexes. This suggests that erythroid cells may contain yet unidentified nuclear factors that may bind to the CCAAT motifs in U3 repeats.

The remaining two conserved sequence motifs TAGCTCA and GGTTTGT in the U3 repeats may also be bound by yet unidentified transcription factors present in erythroid cells. It is of interest to note that motifs similar to TAGCTCA are found also in enhancers and promoters of genes expressed in various hematopoietic lineages: TAGCCTGA in the MLV U3 enhancer, TAGCTAA in the promoter of M-CSF receptor gene and TAGCTTCA in the Invariant Chain promoter of the major histocompatibility complex.

The enhancers of many genes including the HS2 enhancer of the β-globin LCR usually span several hundred bases and are bound by many different protein factors, which make the analysis of the enhancer complex a complicated task. In contrast, the 14 modular U3 repeats in the 5'HS5 LTR contain up to four well conserved DNA motifs and may be bound by similarly limited number of recurrent protein factors, making it a simpler task to analyze the structure of this enhancer complex.

EXAMPLE

This example describes the cloning and characterization of the 5' border region of the LCR upstream of human β-like globin genes.

Materials and Methods

Isolation of 5'ε1.4 phage clone and DNA sequencing: The 5'ε1.4 phage clone spanning 12 kb of DNA 5' of the HS4 site was obtained from a K562 genomic DNA library constructed in EMBL phage (Weber-Benarous et al, 1988). The library was screened with a unique DNA probe 5'ε1.4 located near the HS4 site in the LCR (Li et al, 1985). The genomic DNA insert contained 8 kb of DNA spanning the HS5 site whose sequence was subsequently reported (Yu et al, 1994) and 5 kb of further upstream new DNA. The 8 kb of DNA was cleaved by Hind III into four sub-fragments of 2.7 kb spanning the HS5 site and 1.5, 1.6 and 2 kb spanning the new DNA. They were subcloned into a plasmid vector (Tuan et al, 1990) and sequenced with the dideoxy terminator method (Sanger et al, 1977) using Sequenase or Taquenase Kit (USB Corp). This sequence strategy produced unambiguous DNA sequencing ladders for the entire 8 kb of DNA except for the 1 kb of DNA in the junction area between the 1.5 and 1.6 kb subdlones which contained the repetitive sequences of the ERV-9 LTR. The junction DNA was recloned into a phagemid vector Bluescript II SK(+/−) (Stratagene) and the single stranded DNA was sequenced as above. The sequences were assembled and analyzed using the GCG DNA analysis software. The 8 kb DNA sequence was submitted to GenBank (BankIt 193637 AF064190).

Purification of genomic DNAs from the gorilla and people of different races: Genomic DNAs were isolated anonymously from human blood samples collected by the Hemoglobin Laboratory at the Medical College of Georgia for diagnosis of thalassemia and sickle cell disease. African samples were from patients homozygous for sickle cell disease or Hereditary Persistence of Fetal Hemoglobin (HPFH), Arabic and Asian samples were from people hemizygous for α-thalassemia and the Caucasian samples were from normal individuals or patients with β-thalassemia. The gorilla blood sample was obtained from the Yerkes Primate Center of Emory University. High molecular weight genomic DNAs were purified from nucleated blood cells (Poncz et al, 1982).

PCR-amplification of the 5'HS5 LTR in genomic DNAs and sequence analysis of the amplified LTR: The 5'HS5 LTRs were amplified from genomic DNAs with Primer pair 3 used also for RT-PCR (FIG. 10; forward primer, positions 595–616 and reverse primer 1807–1831, FIG. 2; nucleotides 595 to 616 of SEQ ID NO:1). PCR conditions consist of an initial denaturation at 95° C. for 1.5 min, followed by 32 cycles of denaturation at 95° C. for 1.5 min, annealing at 59° C. for 1 min and extension at 72° C. for 2 min and a final extension step at 72° C. for 15 min. The amplified LTR fragments were purified by Quantum Plasmid Miniprep Kit (Bio-Rad) and sequenced by the Molecular Biology Core Laboratory of the Medical College of Georgia using the cycle sequencing technique with flourescent dideoxy terminators.

Construction of recombinant CAT plasmids: LTR-CAT (Construct 1): The 1 kb LTR was amplified from K562 genomic DNA by PCR with forward primer: 5' TACTGTCGACCTGAGTTTGCTGGGGATG 3' (SEQ ID NO: 23) (positions 3250–3271 in the 8 kb GenBank sequence, BankIt 193637 AF064190 corresponding to positions 595–616 in FIG. 2; nucleotides 595 to 616 in SEQ ID NO:1) and reverse primer 5' GATGGATCCTGTGTCCGGAATTGGTGG 3' (SEQ ID NO: 24)(positions 4282–4299 in GenBank sequence; positions 1677–1694 in FIG. 2; nucleotides 1677 to 1694 in SEQ ID NO:1). A Sal I and a Bam HI cloning site (underlined) were included respectively in the forward and reverse primers. The PCR fragment was cleaved with Sal I and Bam HI enzymes and together with a Bam HI-Hind III adapter was spliced into a promoterless CAT vector derived from εp-CAT (Construct 3) in which the ε-globin promoter (εp) was removed with Sal I and Hind III digestions. Ups-CAT (Construct 2) contains a 1 kb PCR fragment amplified from the genomic DNA located 2 kb further upstream of the LTR and was created with the same cloning strategy. The respective forward and reverse primers were 5' ACTGTCGACTTATGTATTCAAGTTCG 3' (positions 50–66 in GenBank sequence; SEQ ID NO:21) and 5' GATGGATCCAATAGATTTTTGTCATCT 3' (positions 1203–1220 in GenBank sequence; SEQ ID NO:22). εp-CAT (Construct 3) and HS2-εp-CAT (Construct 4) were previously made (Tuan et al, 1989). LTR-εp-CAT (Construct 5) was created with the above 1 kb LTR DNA obtained by PCR which was cleaved at the Sal I and Bam HI cloning sites and spliced into εp-CAT(Construct 3) which was also cleaved at the Sal I and Bam HI sites located 5' of the εp. HS5-εp-CAT (Construct 6) was created with the same cloning strategy as LTR-εp-CAT (Construct 5). The 1.2 kb HS5 fragment was generated by PCR from forward primer 5' ACTGTCGACAAGCTTCTGACAAATTATTCTT 3' (positions 5431–5455, GenBank sequence; SEQ ID NO:15) and reverse primer 5' GATGGATCCACTGAAAGGGCTCATGCAAC 3'(positions 6657–6676), GenBank sequence; SEQ ID NO:16). LTR-HS5-εp-CAT (Construct 7) was made from LTR-εp-CAT (Construct 5) which was linearized at the Bam HI site 3' of the LTR. The above 1.2 kb HS5 fragment obtained by PCR was cleaved at the 5' end with Hind III (a natural site) and at the 3' end with Bam HI and together with a Bam HI-Hind III adapter was spliced into the Bam HI site in LTR-εp-CAT.

Transient and stable transfections and CAT assays: Transfection host cells K562, HL60 and MEL cells were cultured and transfected as described (Tuan et al, 1989) with modifications. In transient transfections, 10 μg of each of the above CAT plasmids were mixed with 5 µg of a reference CMV β-gal plasmid and transfected into the host cells by electroporation. CAT assays were carried out as described (Tuan et al, 1989) with two modified steps of normalizations. The CAT extracts were normalized first with respect to the total protein in the extract determined with the BCA (Bicinchoninic acid) protein kit (Pierce) and then with respect to the β-galactosidase level of the co-transfected CMV β-gal plasmid to ensure that the CAT assays of different samples were carried out on extracts containing similar levels of β-gal activities, therefore, similar amounts of the transfected tested plasmids. The β-gal enzyme levels were determined with the β-gal Assay Kit (Promega). The CAT enzymatic activities were analyzed by thin layer chromatography and quantified with a PhosphorImager (Molecular Dynamics). The results were presented as percentages of conversion calculated from the $^{14}C$ counts in the acetylated chloramphenicol divided by the total input $^{14}C$ counts of the chloramphenicol substrate. In stable transfection, pooled cell populations were studied. The CAT activities were normalized with respect to the copy numbers of the integrated plasmids determined by Southern blots.

Isolation of total cellular RNAs and RT-PCR: Total cellular RNAs were purified from freshly harvested, non-transfected human erythroid K562, promyelocytic HL60, embryonic teratocarcinoma N-Tera (obtained from ATCC) and murine erythroleukemia MEL cell lines, adult human peripheral blood CFU-E and T-lymphocytes (Wickrema et al, 1992) and full term human placenta. The RNAs were purified with the Totally RNA Kit (Ambien). For a semi-quantitative comparison of the RT-PCR bands generated by different primer pairs, each RNA was first reversely transcribed into cDNA with random hexamers as primers into a cDNA master stock, which was then aliquoted into separate tubes for PCR with different primer pairs as described (Kong et al, 1997). The 5'-->3' sequences of the respective forward and reverse primers are marked in FIG. 2. Primer pair 1: CTGAGTTTGCTGGGGATGCGAA (positions 595–616; SEQ ID NO:17) and GATTTAGTGACTCATAT-TGTTTCTGA (positions 1700–1726; SEQ ID NO:18); Primer pair 2: TGCTGCTGCTCACTGTTTGGGTCTA (positions 1349–1373; SEQ ID NO:19) and the reverse primer was the same as that of Primer pair 1. Primer pairs 3 and 4 contain the same forward primers as the respective forward primers of Primer pairs 1 and 2. Primer pairs 3 and 4 contain a common reverse primer: 5'GGGCACTCTGC-CTTAGGGAGTAACA 3' (positions 1807–1831; SEQ ID NO:20). The human β-actin primer pair was obtained from Stratagene. Before RT-PCR, the abilities of the primer pairs to produce amplification fragments were confirmed by PCR with genomic DNA templates.

Results

An LTR-retrotransposon of the ERV-9 family of human endogenous retroviruses is located proximal to the HS5 site in the 5' boundary area of the LCR: In order to study the sequence and function of DNA in the boundary area of the LCR, a K562 DNA library was screened (Weber-Benarous et al, 1988) and obtained a clone containing 8 kb of DNA sequence that spans the HS5 site and 5 kb of new further upstream DNA. As the sequence features of the upstream DNA were previously unknown, the 5 kb new DNA as well as the 3 kb DNA spanning the HS5 site was sequenced (GenBank accession number: BankIt 193637 AF064190). The DNA sequence of the 3 kb DNA spanning the HS5 site is in general agreement with the DNA sequence of this region reported earlier (Yu et al, 1994), except for a number of polymorphic base differences. In the new DNA, sequence matches using the GCG and BLAST programs revealed the existence of a solitary LTR at a location within 2 kb 5' of the HS5 site (Long et al, 1995) (FIG. 1). Comparison with a few selected homologous sequences in the GenBank data base, including the LTR sequence located 5' of the ZNF80 protein gene (Di Cristofano et al, 1995, GenBank Accession No. X83497), showed that the 5'HS5 LTR spans 1.7 kb of DNA (FIG. 2) and belongs to the ERV-9 family of human endogenous retroviruses (La Mantia et al, 1991; Lania et al, 1992).

Figure 2A:
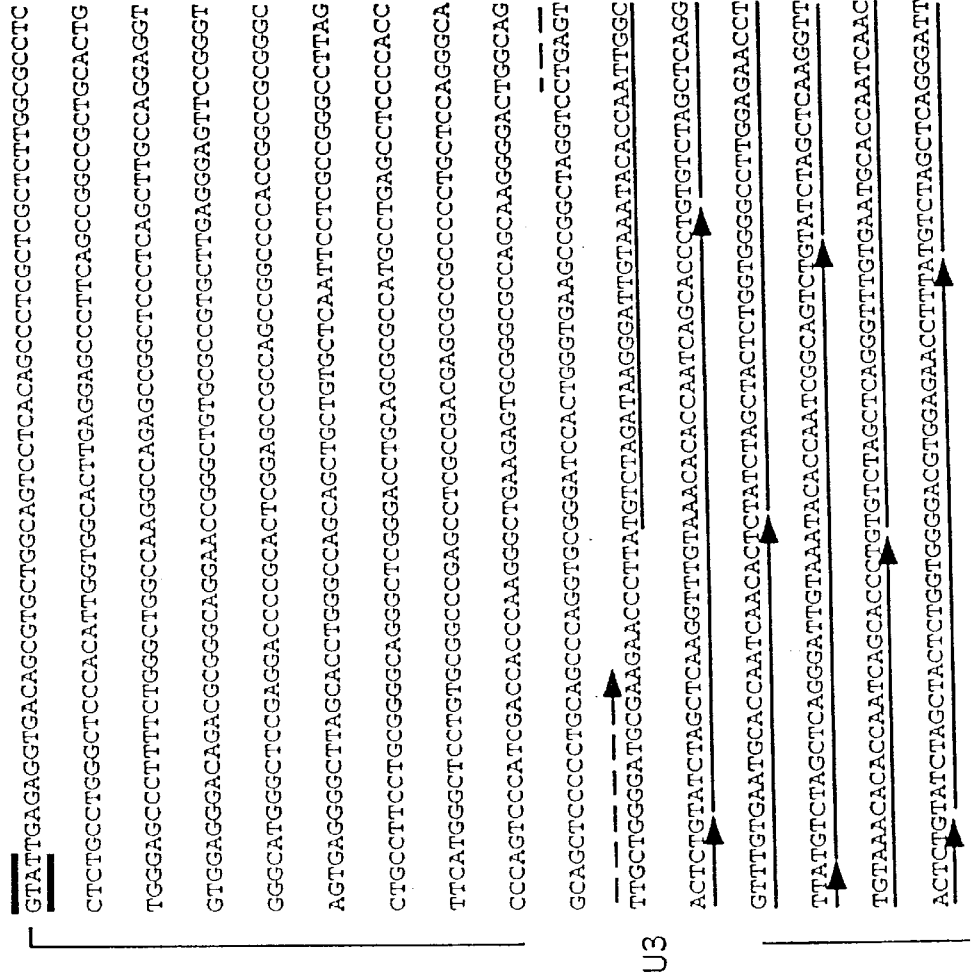

Consistent with a common property of the retrotransposons, the 5'HS5 LTR is flanked by 4 bases of direct repeats GTAT in the genomic DNA immediately 5' and 3' of the LTR sequence (FIG. 2). This indicates that the 5' HS5 LTR was inserted into the human ancestral genome at the GTAT site sometime during evolution. In line with the general LTR structure of mammalian retroviruses (Temin, 1982), the 5'HS5 LTR contains the U3, R and U5 regions and is bracketed by the dinucleotides TG and CA respectively at the 5' and 3' ends (FIG. 2). The U3 region contains the viral enhancer spanning tandemly repeated DNA sequences and the viral promoter (Lenz et al, 1984; Golemis et al, 1990; La Mantia et al, 1991; Anagnou et al, 1995). The R region starts with the viral transcription initiation site (La Mantia et al, 1992) and is followed by the U5 region (FIG. 1). In the U3 region, the 600 DNA bases preceding the U3 repeats are comprised of 70% G and C bases. This GC-rich region is found in many of the homologous ERV-9 LTRs in the data base but is not present in the LTR of the ERV-9 provirus (La Mantia et al, 1991). The U3 enhancer repeats and the promoter in the 5'HS5 LTR show 80–90% base identities with other ERV-9 LTRs found in the human genome (Yang et al, 1983; La Mantia et al, 1991; Lania et al, 1992; Di Cristofano et al, 1995).

It is of interest to note that in addition to the 5'HS5 LTR located approximately 25 kb 5' of the ε-globin gene, another ERV-9 LTR is located at a position approximately 25 kb 3' to the β-globin gene (FIG. 1). The repetitive DNA in the region 3' of the β-globin gene was first reported by Henthorn et al (1986) and subsequently studied by Anagnou et al (1995). Although neither of those groups recognized that the repetitive DNA was part of an endogenous LTR, sequence matches as shown above revealed that the repetitive DNA of this region bears sequence identities of 80–90% with the U3, R and U5 regions of the 5'HS5 LTR. Thus, two copies of the ERV-9 LTRs exist in flanking positions of the β-globin gene cluster.

Sequence analysis of the U3 enhancer region in the 5' HS5 ERV-9 LTR: The U3 enhancer region of the 5' HS5 LTR shows an interesting sequence structure. It is comprised of fourteen tandem repeats of a consensus DNA sequence of 37–41 bases (FIG. 2). Sequence matches show that the tandem repeats are comprised of four subtypes 1, 2, 3 and 4, which are arranged in the LTR in the order 1-2-3-4-1-2-3-4-1-2-3-4-4-1 (FIG. 3). Among the four subtypes, the sequence identities are 60–80%, using subtype 2 as the reference. Among the U3 repeats of each subtype, the sequence identities are 80–98% (FIG. 3). The consensus sequence of the fourteen U3 repeats (FIG. 3) reveals recurrent sequence motifs that can potentially bind to the GATA (Ko and Engel, 1993); Merika and Orkin, 1993), CCAAT (Johnson and McKnight, 1989) and CACCC (Miller and Bieker, 1993; Crossley et al, 1996) transcription factors. Altogether, the U3 enhancer region contains within 600 bases DNA eight GATA, nine CCAAT, three CACCC and four CCACC sites. The consensus sequence of the fourteen U3 repeats shows higher than 90% sequence identity with that of the seven U3 repeats in the 3'β LTR (Henthorn et al, 1986) and of the six U3 repeats in LTR2, a random clone of the ERV-9 LTR (Lania et al, 1992) (FIG. 3).

Figure 4:
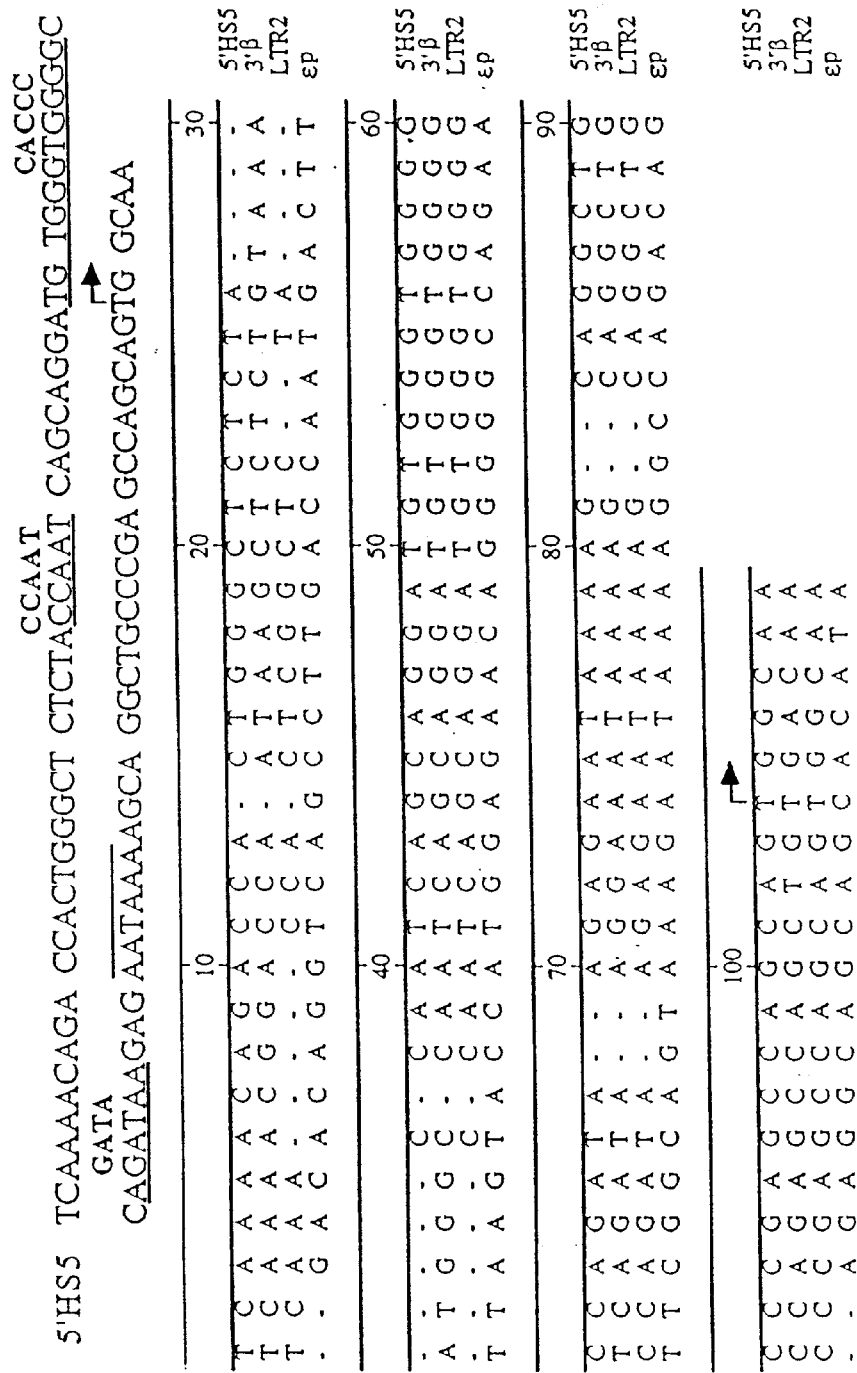
FIG. 4 is a sequence comparison of three U3 promoters and the ε-globin promoter. At the top is the U3 promoter of the 5'HS5 LTR (nucleotides 1194 to 1287 of SEQ ID NO:1). The overlined bases are the equivalent of the TATA box (Strazzullo et al, 1994). Underlined bases are the DNA motifs found also in the U3 repeats. Angled arrow is the transcriptional initiation site in LTR2 (La Mantia et al, 1992; Strazzullo et al, 1994) and the presumed transcriptional initiation site in the 5'HS5 LTR. At the bottom is the sequence alignment of the four promoters in the 5'HS5 LTR (nucleotides 1194 to 1287 of SEQ ID NO:1) 3'β LTR (SEQ ID NO:2) LTR2 (SEQ ID NO:3), and εp (SEQ ID NO:4), respectively. Dashes are DNA base deletions.

Sequence analysis of the U3 promoter region: The promoter sequence in the LTR is located in the U3 region at the 3' end of the fourteen U3 repeats. It is located immediately upstream of the R region whose 5' border marks the transcriptional initiation site for retroviral RNA synthesis (Temin, 1982) (FIG. 3). The promoter of the 5'HS5 LTR shows a sequence homology of 80% with the promoter of the 3'β LTR and of over 90% with the promoter of LTR2 (FIG. 4). The transcriptional initiation site of LTR2 has been determined by primer extension to be located 28 bases downstream of the AATAAAA box (La Mantia et al, 1992; Strazzullo et al, 1994). Because of extensive sequence identities between the 5'HS5 LTR and the LTR2 promoters, especially the 100% sequence homology in the 70 DNA bases flanking the AATAAAA box, the presumptive transcriptional initiation site of the 5'HS5 LTR was placed at the identical T base 28 bases downstream of the AATAAAA box (FIG. 4). All three LTR promoters contain the GATA, CACCC and CCAAT motifs located at identical locations, -36, -46 and -63 bases respectively, relative to the retroviral transcriptional initiation site (FIG. 4).

The 5'HS5 LTR promoter also bears structural similarities with the promoters of the further downstream ε-, γ- and β-globin genes (Baralle et al, 1980; Shen et al, 1981; Poncz et al, 1983; Li et al, 1985) in that a combination of similar GATA, CACCC and CCAAT motifs is found also upstream of the AATAAAA boxes in the globin promoters (Nienhuis et al, 1984). In particular, the LTR promoter and the ε-globin promoter share additional sequence identities in the region immediately 5' of the transcriptional initiation site (FIG. 4). The above sequence and structural homologies suggest that, like the globin promoters, the 5'HS5 LTR promoter would be active in erythroid cells.

The 5' HS5 ERV-9 LTR is conserved in the genomes of the gorilla and of people of different racial lineages: As the 5'HS5 LTR is apparently a retrotransposon and is located not near but far upstream of the β-like globin genes, it was possible that the 5'HS5 LTR might have resulted from a recent insertional event in the K562 genome during cell culture and did not serve a relevant cellular function. However, were this the case, the 5'HS5 LTR would not be present in the genome of the gorilla which diverged from the human genome approximately 10 million years ago (Sibley and Ahlquist, 1987) nor in the genomes of people of different racial lineages which diverged approximately 100,000 years ago (Vogel and Motulsky, 1986). To examine this issue, PCR was used to detect the presence or absence of the 5'HS5 LTR in the genomic DNAs isolated from the blood samples of the gorilla and people of different races. The PCR primers were synthesized according to the K562 DNA sequence, which amplified 1.2 kb of 5'HS5 LTR including 130 bases of genomic DNA downstream of the LTR (see Methods and FIG. 2).

The PCR results indicate that the 5'HS5 ERV-9 LTR is conserved in the genomes of the gorilla and people across racial lines. Fifteen out of a total of 17 human DNAs isolated from Africans, Arab, Asian and Caucasians and from human cell lines K562 and HL60 produced amplicons of the anticipated length of 1.2 kb. However, two of the nine African DNAs produced either a shorter amplicon of 1.1 kb or both a longer 1.4 kb and a shorter 1.1 kb amplicons, while the gorilla DNA produced an even shorter amplicon of 0.9 kb (FIG. 6).

Figure 5A:
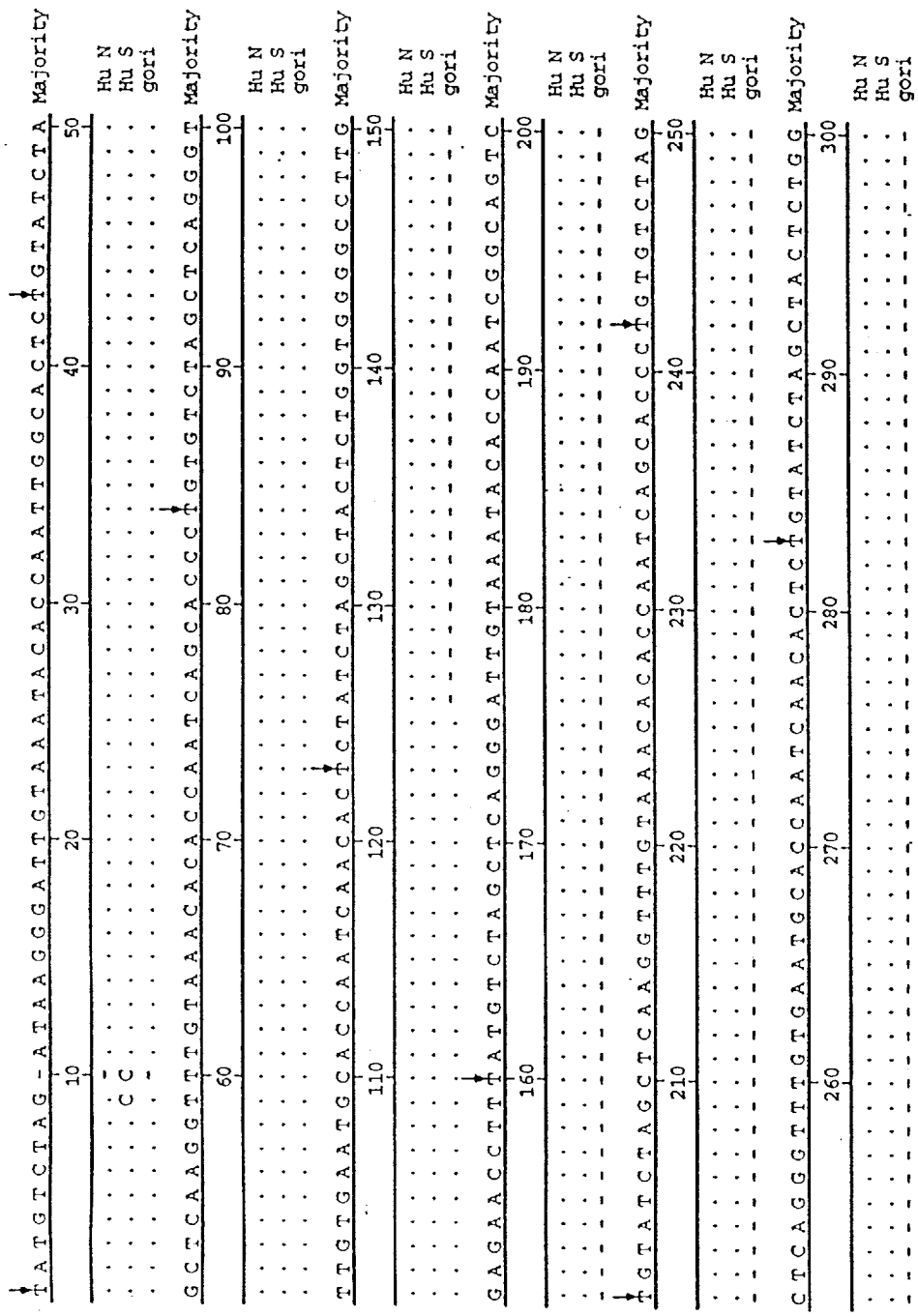
Figure 5B:
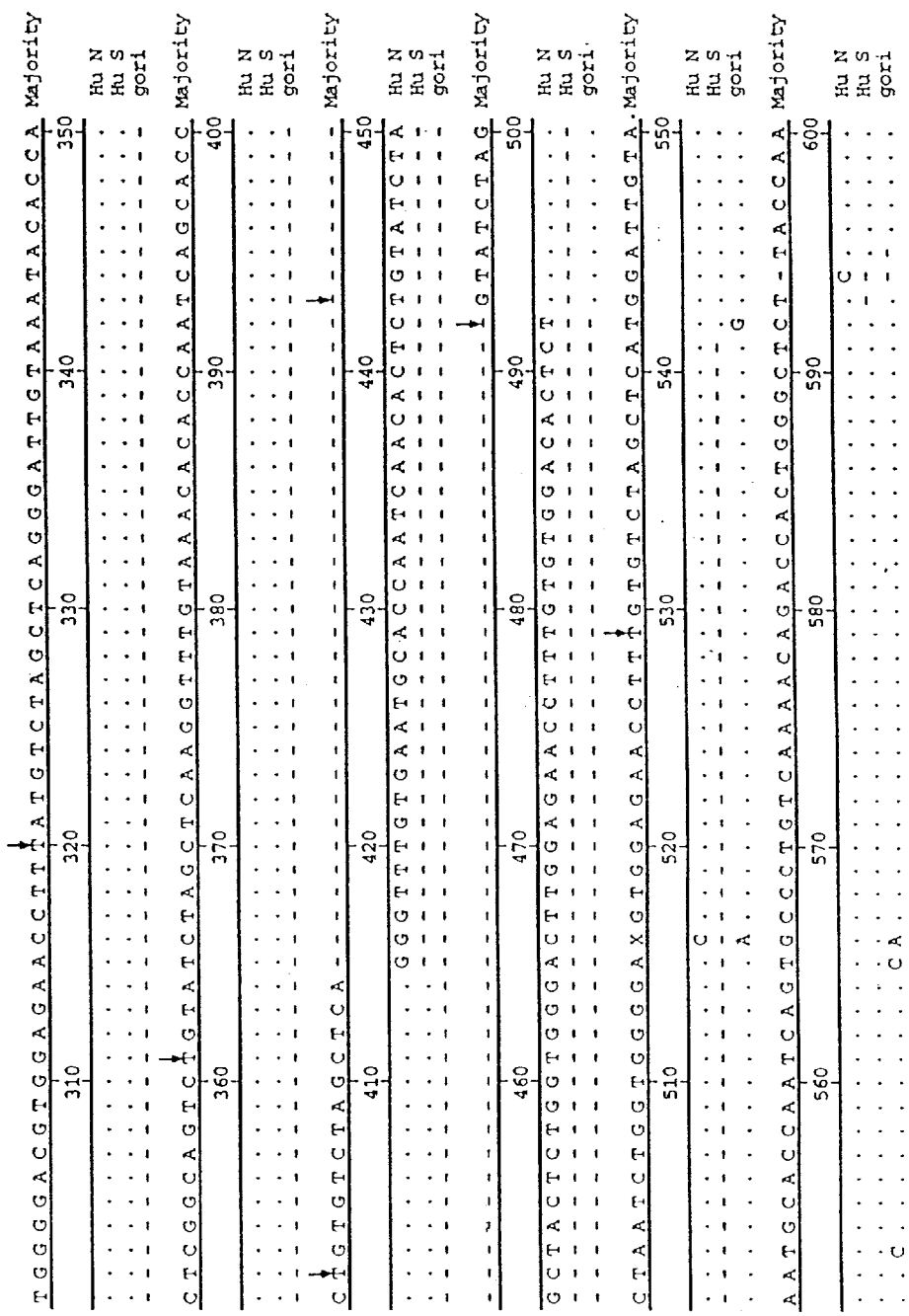
Figure 5C:
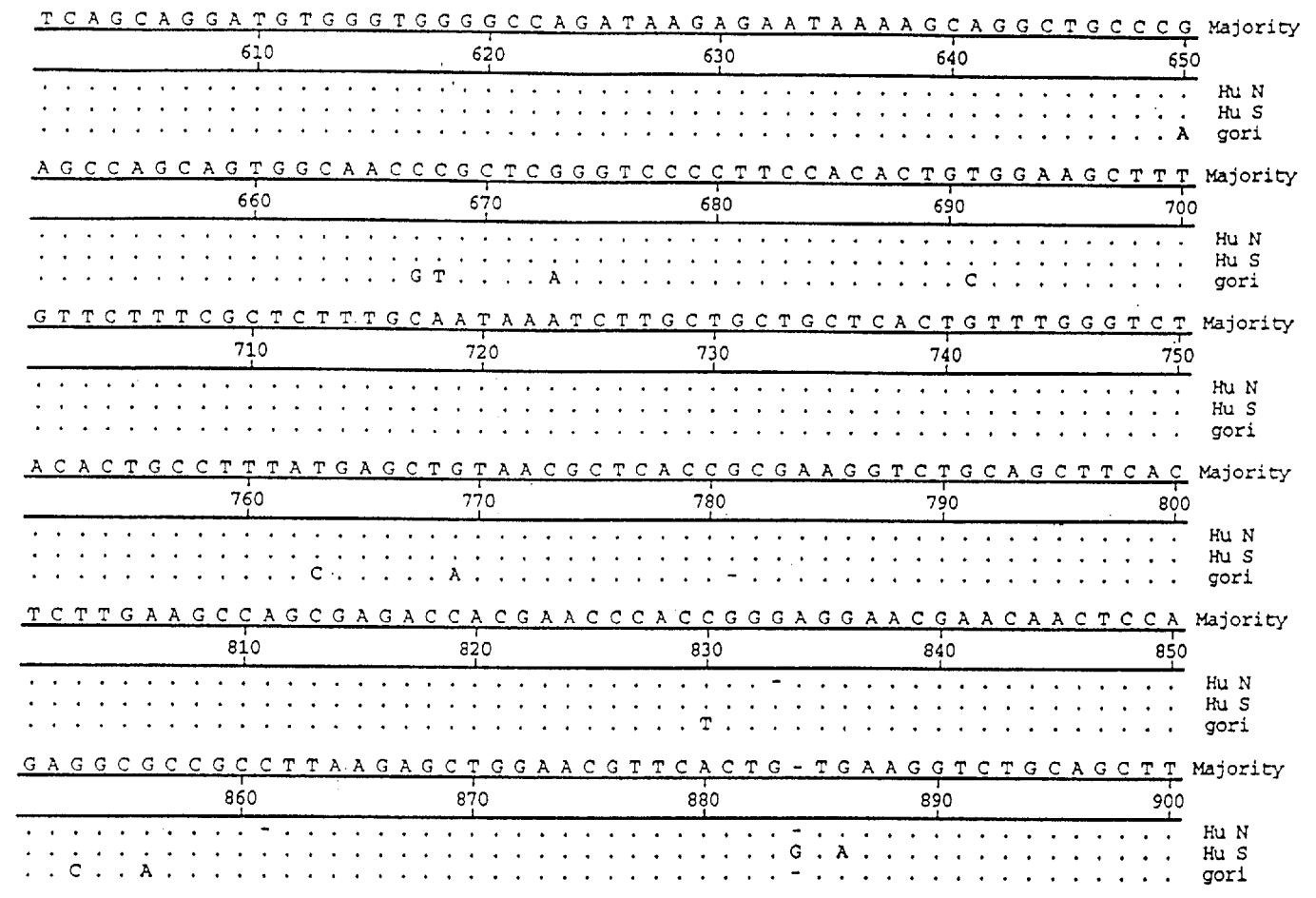
Figure 5D:
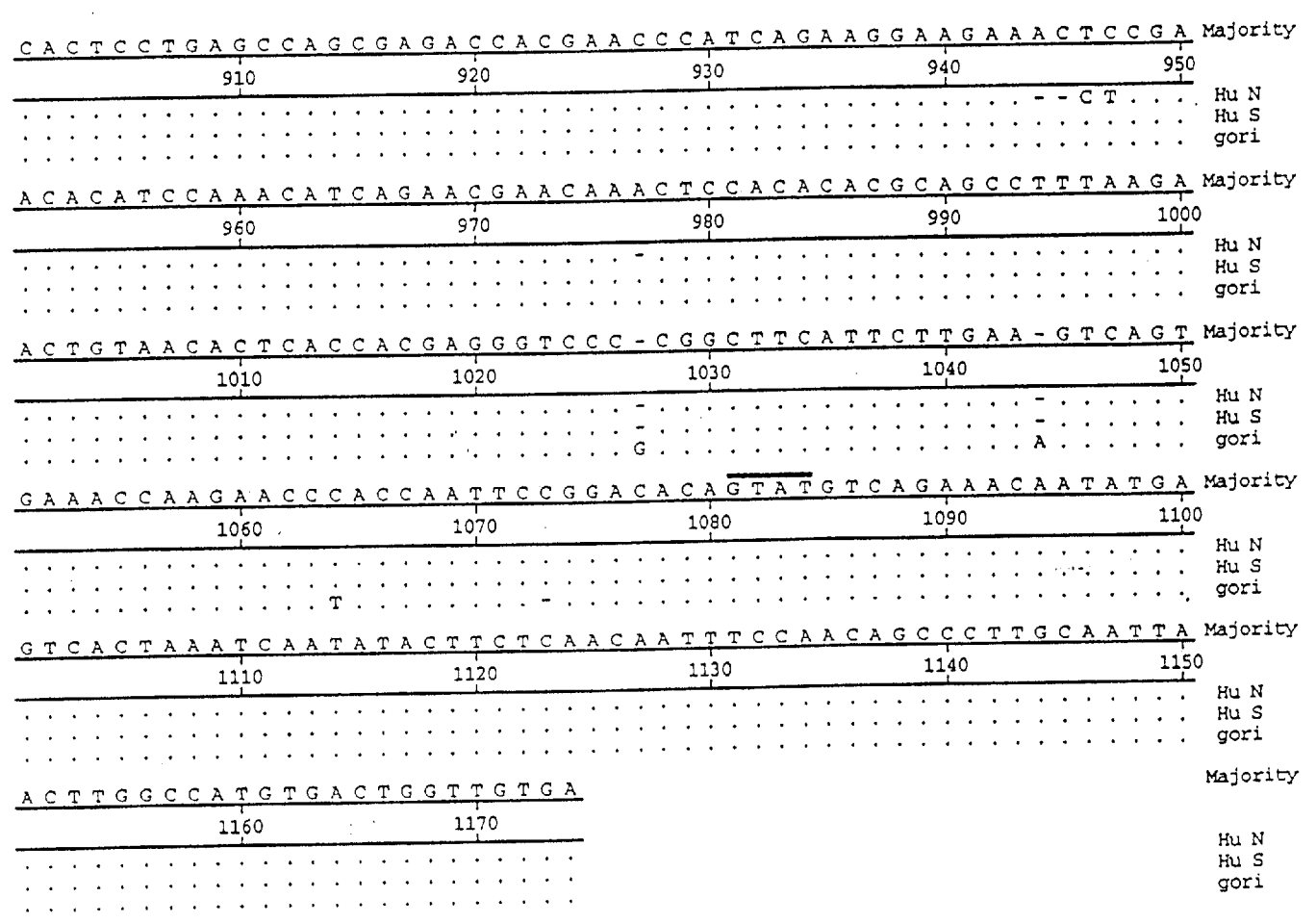

It was possible that the observed amplicons might be spurious PCR products amplified by the primer pair from other ERV-9 LTRs in the human or the gorilla genome, since the 5' primer was located within the U3 region immediately upstream of the enhancer repeats—a region present also in some of the other ERV-9 LTRs even though the 3' primer was located in the unique genomic DNA region (see FIG. 2). Therefore, the authenticity of the amplicons was further confirmed by DNA sequencing. Four standard amplicons of 1.2 kb from two Caucasian and two African DNAs, two shorter amplicons of 1.1 kb from the African DNAs, and the 0.9 kb amplicon of the gorilla DNA were sequenced (FIG. 5). The electropherograms of the DNA sequences showed sharp DNA sequence ladders with only a couple of ambiguities where two different bases occupied the same sequence positions, indicating that the two homologous chromosomes contained base polymorphism at these positions. All the sequenced amplicons showed base identities of 98–99% in both the LTR and the 3' flanking genomic DNA; the only exception was the fewer number of U3 repeats in some people and in the gorilla (FIGS. 5 and 6). If the sequenced amplicons contained amplification products generated also from other homologous ERV-9 LTRs, the electropherograms would have contained too many sequence ambiguities to generate clearly readable sequences. The above observations indicate that the amplicons were genuine products of the 5'HS5 LTR in the human and gorilla genomes.

Figure 6:
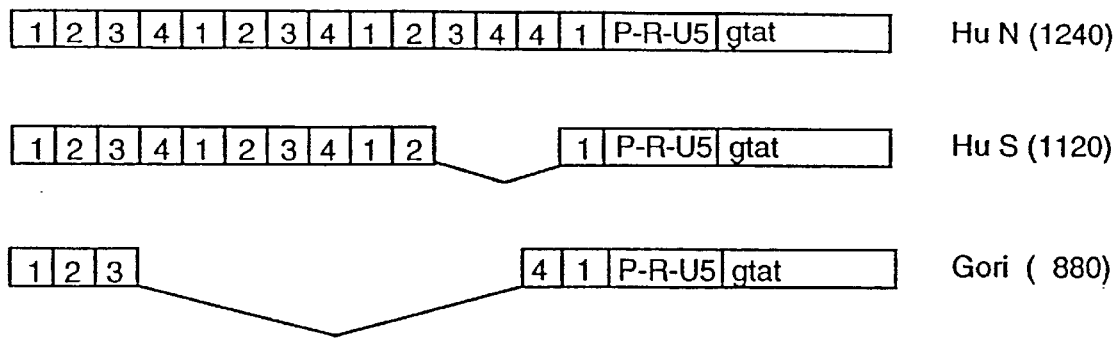
FIG. 6 is a diagram comparing the structures of the 5'HS5 LTR in the genomes of human and gorilla and in people of different racial lineages. Hu N is the human LTR of the normal length with 14 U3 repeats. Hu S is the human LTR of a shorter length with 11 U3 repeats. Gori is the gorilla LTR with 5 U3 repeats. Numbers in parentheses are the total number of bases in the LTRs including 140 bases of genomic DNAs downstream of the LTR insertion site—the GTAT bases, that were amplified by the PCR primers. Bent lines in Hu S and Gori are deletions of three and nine complete U3 repeats in the truncated human and gorilla LTRs respectively.

In both the shorter human amplicons containing eleven U3 repeats, the deletion of three complete U3 repeats was generated apparently by the same in phase deletion event so the subtype organizations of both amplicons were identical, 1-2-3-4-1-2-3-4-1-2-1, (FIGS. 5 and 6). In the gorilla amplicon with five U3 repeats, the subtype organization is 1-2-3-4-1 (FIGS. 5 and 6). The apparent genomic insertion site of the LTR—the GTAT sequence is conserved in both the human and gorilla amplicons (FIG. 5).

The remarkable sequence identities in the 5'HS5 LTR between human and gorilla and among people of different races indicate that this LTR was probably inserted into the 5' boundary area of the β-globin LCR at least 10 million years ago before the divergence of the human and apes and it has been conserved in the genomes of the higher primates during the ensuing years of evolution. These observations indicate that this 5'HS5 LTR-retrotransposon is likely conserved for the preservation of a relevant cellular function of the host.

The 5'HS5 LTR ERV-9 LTR possesses enhancer and promoter activities in erythroid cells: To demonstrate that the enhancer and promoter regions in the 5'HS5 LTR possess enhancer and promoter activities, seven recombinant CAT plasmids were made (FIG. 7). LTR-CAT (Construct 1) contained the 1 kb LTR spanning the 14 U3 enhancer repeats, U3 promoter, R and U5 spliced 5' of the CAT gene in the absence of a promoter in the vector. To determine whether other regions of the 5' boundary area of the LCR also possessed enhancer and promoter activities, the control Ups-CAT plasmid (Construct 2) contained a 1 kb DNA (Ups) located further upstream of the LTR (FIG. 1). The HS2-εp-CAT plasmid (Construct 4) that contained the strong HS2 enhancer of the LCR (Tuan et al, 1989) coupled to the ε-globin promoter (εp) served as the standard with which to compare the enhancer and promoter activities of the 5'HS5 LTR. To test if the enhancer in 5'HS5 LTR can synergize with and activate the HS5 site located naturally downstream of and proximal to the LTR, LTR-εp-CAT, HS5-εp-CAT and LTR-HS5-εp-CAT (Constructs 5, 6 and FIG. 7) contained respectively the LTR and HS5 site spliced either separately or together into εp-CAT (Construct 3). The plasmids were transiently transfected into erythroid K562 and MEL cells and nonerythroid HL60 cells and stably integrated into K562 cells.

Figure 8:
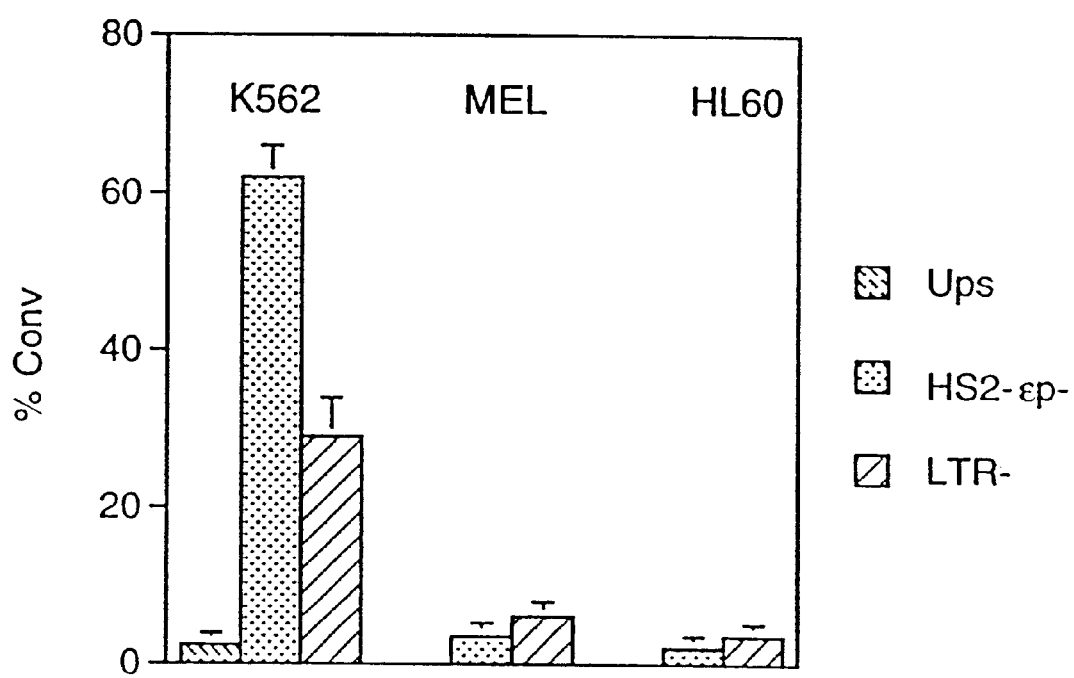
FIG. 8 is a graph of enhancer and promoter activities (in percent of substrate converted) of the 5'HS5 LTR in recombinant CAT constructs Ups-CAT, HS2-εp-CAT and LTR-CAT plasmids transiently transfected into K562, MEL and HL60 cells. Percent Conv is percentage conversion of the $^{14}$C-chloramphenicol substrate by the CAT enzyme produced by the transfected test plasmid after normalization with respect to a common level of a co-transfected CMV-β-gal plasmid.

Transient transfection results indicate that in human erythroid K562 cells, the LTR in LTR-CAT plasmid displayed enhancer and promoter activities that were approximately 50% of the combination of the HS2 enhancer and the ε-globin promoter in the HS2-εp-CAT plasmid. In contrast, in murine erythroid MEL cells and human nonerythroid HL60 cells, both LTR-CAT and HS2-εp-CAT displayed much lower enhancer and promoter activities (FIG. 8). The low enhancer activity of the HS2 enhancer in MEL cells was due apparently to the inactivity of the cis-linked embryonic ε-globin promoter in MEL cells expressing the adult globin program; when linked to the more permissive adult β-globin promoter, the HS2 enhancer displayed much higher enhancer activity in MEL cells (Cavallesco and Tuan, 1997). Likewise, the U3 enhancer in the LTR may also be potentially active in MEL cells; its apparently low enhancer activity may be due to the low activity in MEL cells of the U3 promoter which shares certain sequence identities with the δ-globin promoter (FIG. 4).

Figure 9:
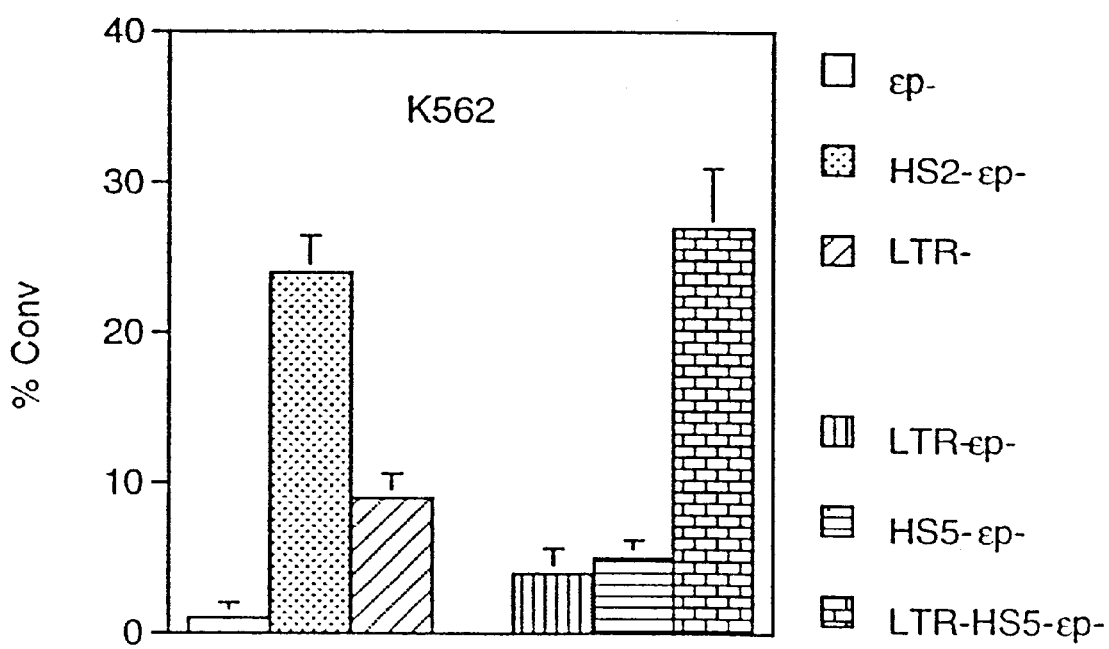
FIG. 9 is a graph of enhancer and promoter activities (in percent of substrate converted) of the 5'HS5 LTR in recombinant CAT plasmids εp-CAT, HS2-εp-CAT, LTR-CAT, LTR-εp-CAT, HS5-εp-CAT and LTR-HS5-εp-CAT integrated into the genome of K562 cells. Percent Conv is the percentage conversion of the $^{14}$C-chloramphenicol substrate by the CAT enzyme produced by the integrated plasmids after normalization with respect to the per cell copy numbers of the plasmids.

When stably integrated into the genome of K562 cells, the LTR displayed enhancer and promoter activities that were approximately 30% of those of the HS2-εp-CAT plasmid (FIG. 9). However, in integrated LTR-HS5-εp-CAT plasmid, the LTR enhancer synergized with the HS5 site and activated the CAT gene to a level comparable to that displayed by the HS2 enhancer in HS2-εp-CAT (FIG. 9). These results indicate that the 5'HS5 LTR possesses enhancer and promoter activities in erythroid cells and it synergized with and activated the HS5 site.

The endogenous 5'HS5 LTR activates the transcription of downstream DNA preferentially in erythroid cells: It was next determined if the endogenous 5'HS5 LTR also exhibits enhancer and promoter activities and can activate the transcription of the downstream R region and the flanking genomic DNA in the β-globin LCR. The transcriptional statuses of the 5'HS5 LTR and downstream genomic DNA were determined by RT-PCR in erythroid K562 and nonerythroid T-lymphocytes and placental cells.

Figure 10:
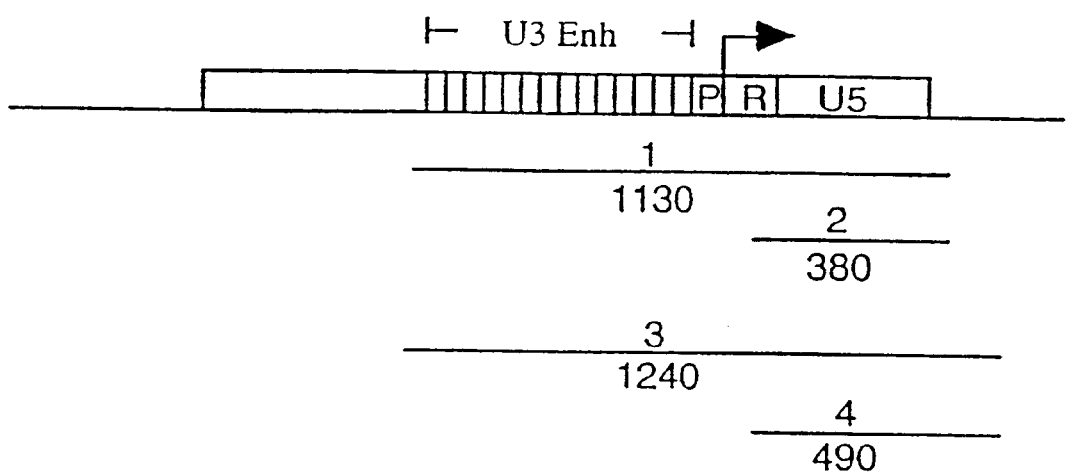
FIG. 10 is a diagram of the 5'HS5 LTR in normal human DNA with 14 U3 enhancer repeats. The four horizontal lines 1, 2, 3 and 4 represent the anticipated RT-PCR fragments amplified respectively by Primer pairs 1–4, synthesized according to the K562 sequence in FIG. 2. Numbers below the lines are the anticipated sizes in base pairs of the amplified cDNA fragments.

Four PCR primer pairs were made (FIG. 10). Primer pair 1 was synthesized to determine if the entire LTR between the U3 enhancer and the U5 regions as well as the genomic DNA immediately downstream of it was transcribed. Primer pair 2 was synthesized to detect retroviral mRNA transcripts of the R and U5 regions whose synthesis was activated by the U3 enhancer and promoter. In order to ensure that Primer pair 2 detected the RNA transcribed specifically from the 5'HS5 LTR and not RNAs transcribed from other ERV-9 LTRs, the forward Primer was located in the R region that contains a number of polymorphic bases among the ERV-9 LTRs FIG. 2; Henthorn et al, 1986 and Lania et al, 1992) and the reverse primer is located in the genomic DNA immediately downstream of the LTR. Primer pairs 3 and 4 were synthesized to confirm that the RNAs detected by Primer pairs 1 and 2 were indeed transcribed from 5'HS5 ERV-9 LTR. These two primer pairs contained the same two respective forward primers as Primer pairs 1 and 2 but shared a common reverse primer located in the genomic DNA 110 bases further downstream of the reverse primer of Primer pairs 1 and 2. Hence, the authentic RT-PCR bands of the 5'HS5 LTR generated by these primer pairs would be 110 bases longer than those generated respectively by Primer pairs 1 and 2 (FIG. 10).

Consistent with the design of the primer pairs (FIG. 10), the sizes of the RT-PCR bands produced by Primer pairs 3 and 4 were indeed longer by 110 bases than those produced by Primer pairs 1 and 2. This indicates that the RT-PCR bands generated by Primer pairs 1–4 were genuine products amplified from the 5'HS5 LTR and not from other ERV-9 LTRs in the human genome. In addition, the authenticity of the PCR band produced by Primer pair 3 had been confirmed by direct DNA sequencing (FIG. 5).

For a semi-quantitative comparison of the intensities of RT-PCR bands generated by primer pairs 1–4 in different RNA samples, a β-actin primer pair spanning a region in the ubiquitous β-actin mRNA assumed to be expressed at a constant level in different cell types was included in the RT-PCRs. Consistent with this assumption, the intensities of the β-actin band generated by the same amount of different RNAs were similar. The relative intensities of the LTR bands with respect to the intensity of the β-actin band generated from aliquots of the same cDNA master stock as the LTR bands (see Methods) were then compared.

The RT-PCR results indicate that the endogenous 5'HS5 LTR promoted the transcription of the R and U5 regions. In both erythroid and nonerythroid cells, Primer pairs 2 and 4 generated amplification bands of the R and U5 regions. However, the LTR enhancer and promoter appear to be more active in erythroid than in nonerythroid cells, as the amplification bands generated from RNAs of K562 cells and CFU-E were relatively stronger than those of nonerythroid T-lymphocytes, N-Tera and HL60 cells. An apparent exception to the above observation was the nonerythroid placenta which also generated strong LTR bands. This may be due to contamination in placenta of abundant maternal and fetal blood erythroid cells in which the 5'HS5 LTR enhancer and promoter were active. On the other hand, the 5'HS5 LTR enhancer and promoter may also be active in the placenta since many HERVs and their solitary LTRs have been found to be capable of initiating viral RNA synthesis from the R region in placental cells (Wilkinson et al, 1994; Lower et al 1996).

Further upstream of the R region in the LTR, no additional transcriptional initiation sites appear to exist in the majority of the cell types tested, since Primer pairs 1 and 3 did not generate detectable bands from RNAs of erytliroid K562 and nonerythroid T-lymphocytes, N-Tera and HL60 cells. However, Primer pairs 1 and 3 generated faint amplification bands from erythroid CFU-E and nonerythroid placenta RNAs. This suggests that CFU-E and placenta may contain additional transcriptional initiation sites proximal to the 5'HS5 LTR.

The above RT-PCR results indicate that the endogenous 5'HS5 LTR possesses apparent enhancer and promoter activities and is capable of promoting the transcription of the R and U5 regions in the LTR and of further downstream genomic DNA in the LCR.

Disscussion

This example shows that a solitary ERV-9 LTR with the characteristics of a retrotransposon is located proximal to the HS5 site in the apparent 5' boundary area of the β-globin LCR. This 5' HS5 ERV-9 LTR possesses unusual sequence features in the multiple tandem repeats of the U3 enhancer region. The U3 repeats and the immediately downstream U3 promoter contain within 700 DNA bases nine GATA, four CACCC and ten CCAAT sites. These DNA motifs can bind respectively to the cognate GATA (Orkin, 1992) and CACCC (Miller and Bieker, 1993; Crossley et al, 1996) transcription factors expressed abundantly in erythroid cells and to the CCAAT factors C/EBP (Johnson and McKnight, 1989) and NF-Y (Bi et al, 1997), expressed in many hematopoietic and nonhematopoietic cells. The high concentration of these motifs in the U3 region suggests that the 5'HS5 ERV-9 LTR may be preferentially active in erythroid cells.

The 5'HS5 LTR is conserved in the gorilla and in people of different racial lineages, indicating that this LTR was probably inserted into its location at the 5' boundary area of the LCR before species divergence between human and gorilla approximately 10 million years ago. The conservation of the 5'HS5 LTR during evolution of the higher primates suggests that this LTR-retrotransposon may serve a relevant cellular function of the host.

Functional tests with the CAT reporter gene assays show that the 5'HS5 LTR, in line with its component sequence motifs, possesses enhancer and promoter activities preferentially in erythroid cells. Moreover, the LTR enhancer activity can synergize with and activate the cis-linked HS5 site in the LCR.

REFERENCES

Anagnou, N. P., Perez-Stable, C., Gelinas, R., Constantini, F., Liapaki, K., Constantopoulou, M., Kosteas, T., Moschonas, N. K., and Stamatoyannopoulos, G. (1995). Sequences Located 3' to the Breakpoint of the Hereditary Persistence of Fetal Hemoglobin-3 Deletion Exhibit Enhancer Activity and Can Modify the Developmental Expression of the Human Fetal Aγ-Globin Gene in Transgenic Mice. *J. Biol. Chem* 270:10256–10263.

Ashe, H., Monks, J., Wijgerde, M., Fraser, P. and Proudfoot, N. (1997). Intergenic transcription and transinduction of the human β-globin locus. *Genes & Dev.* 11, 2494–2509.

Baralle, F., Shoulders, C., and Proudfoot, N. (1980). The primary structure of the human ε-globin gene. *Cell* 21, 621–626. Bi, W., Wu., L., Coustry, F., Crombrugghe, B. and Maity, S. (1997). DNA binding specificity of the CCAAT-binding factor CBF/NF-Y. *J. Biol. Chem.* 272,26562–26572.

Cavallesco, R. and Tuan, D. (1997). Modulatory subdomains of the HS2 enhance differentially regulate enhancer activity in erythroid cells at different developmental stages. *Blood Cells, Molecules and Diseases* 23, 8–26. (World-wide web URL:http//www.scripps.edu/bcmd).

Chung, J. H., Whiteley, M. & Felsenfeld, G. (1993). A 5' element of the chicken β-globin domain serves as an insulator in human erythroid cells and protects against position effect in Drosophila. Cell 74, 505–514.

Coffin, J. (1984). Endogenous retroviruses. In "RNA tumor viruses" (R. Weiss, N. Teich, H. Varmus, and J. Coffin, eds), Vol. 1, pp. 1109–1203, Cold Spring Harbor Laboratory, N.Y.

Crossley, M., Whitelaw, E., Perkins, A., Williams, G., Fujiwara, Y., and Orkin, S. (1996). Isolation and characterization of the cDNA encoding BKLF/TEF-2, a major CACCC-box-binding protein in erythroid cells and selected other cells. *Mol. Cell. Biol.* 16, 1695–1705.

Dhar, V., Nandi, A., Schildkraut, C. L., & Skoultchi, A. I. (1990). Erythroid-specific nuclease-hypersensitive sites flanking the human β-globin domain. *Mol. Cell. Biol.* 10, 4324–4333.

DiCristofano, A., Strazzullo, M., Longo, L., and LaMantia, G. (1995). Characterization and genomic mapping of the ZNF80 locus: expression of this zinc-finger gene is driven by a solitary LTR of ERV9 endogenous retroviral family. *Nucleic Acids Research* 23, 2823–2830.

DiCristofano, A., Strazzullo, M., Parisi, T., and LaMantia, G. (1995). Mobilization of an ERV9 Human Endogenous Retroviral Element during Primate Evolution. *Virology* 213, 271–275.

Doolittle, W. and Sapienza, C. (1980). Selfish genes, the phenotype paradigm and genome evolution. *Nature* 284, 601–603.

Efstratiadis, A., Posakony, J. W., Maniatis, T., Lawn, R. M., O'Connell, C., Spritz, R. A., DeRiel, J. K., Forget, B. G., Weissman, S. M., Slightom, J. L. Blechl, A. E., Smithies, O., Baralle, F. E., Shoulders, C. C., & Proudfoot, N. J. (1980). The structure and evolution of the human β-globin gene family. *Cell* 219 653–668.

Fan, H. (1994). Retroviruses and their role in cancer. In "The Retroviridae" (J. Levy ed), Vol. 3, pp. 313–362, Plenum Press, N.Y.

Feuchter, A. E., Freeman, J. D., and Mager, D. L. (1992). Strategy for Detecting Cellular Transcripts Promoted by Human Endogenous Long Terminal Repeats: Identification of a Novel Gene (CDC4Lease) with Homology to Yeast CDC4. *Genomics* 13, 1237–1246.

Feuchter-Murthy, A. E., Freeman, D. J., and Mager, D. L. (1993) Splicing of a human endogenous retrovirus to a novel phospholipase A2 related gene. *Nucleic Acids Research* 21, 135–143.

Forrester, W. C., Takegawa, S., Papayannopoulou, T., Stamatoyannopoulos, G., & Groudine, M. (1987). Evidence for a locus activation region: the formation of developmentally stable hypersensitive sites in globin-expressing hybrids. *Nucl. Acids Res.* 15, 10159–10177.

Golemis, E. A., Speck, N. A., and Hopkins, N. (1990). Alignment of U3 Region Sequences of Mammalian Type C Viruses: Identification of highly conserved motifs and implications for enhancer design. *Journal of Virology* 64:534–542.

Goodchild, N., Wilkinson, D. A., and Mager, D. L. (1992). Human endogenous long terminal repeat provides a polyadenylation signal a novel, alternatively spliced transcript in normal placenta. *Gene* 121, 287–294.

Grosveld, F., Assendelft, G. B. V., Greaves, D. R., & Kollias, G. (1987). Position-independent, high-level expression of the human β-globin gene in transgenic mice. *Cell* 51, 975–985.

Hardison, R., Slightom, J., Gumucio, D., Goodman, M. Stojanovic, N. and Miller, W. (1997). Locus Control Regions of mammalian β-globin gene cluster: combining phylogenetic analyses and experimental results to gain functional insights. *Gene* 205: 73–94.

Henikoff, S., Greene, E., Pietrokovski, S., Bork, P., Attwood, T. and Hood, L. (1997). Gene families: The taxonomy of protein paralogs and chimeras. *Science* 278, 609–614.

Henthorn, P., Mager, D., Huisman, H. and Smithies, O. (1986). A gene deletion ending within a complex array of repeated sequences 3' to the human β-globin gene cluster. *Proc. Natl. Acad. Sci. USA* 83, 5194–5198.

Jarman, A. P. & Higgs, D. R. (1988). Nuclear scaffold attachment sites in the human globin gene complexes. *EMBO J* 7, 3337–3344.

Johnson, P. and McKnight, S. (1989). Eukaryotic transcriptional regulatory proteins. *Annual Rev. Biochem.* 58, 799–839.

Kellum, R. & Schedl, P. (1991). A position-effect assay for boundaries of higher order chromosomal domains. *Cell*, 64, 941–950.

Keshet, E., Schkff, R., Itin, A. (1991). Mouse retrotransposons: a cellular reservoir of long terminal repeat (LTR) elements with diverse transcriptional specificities. *Adv. Cancer Res.* 56, 215–251.

Ko, L. J., & Engel, J. D. (1993). DNA-binding specificities of the GATA transcription factor family. *Mol. Cell. Biol.* 13, 4011–4022.

Kong, S., Bohl, D., Li, C. and Tuan, D. (1997). Transcription of the HS2 enhancer toward a cis-linked gene is independent of the orientation, position, and distance of the enhancer relative to the gene. *Mol. Cell. Biol.* 17, 3955–3965.

LaMantia, G. Pengue, G., Maglione, D., Pannuti, A., Pascucci, A., and Lania, L. (1989). Identification of new human repetitive sequences: characterization of the corresponding cDNAs and their expression in embryonal carcinoma cells. *Nucleic Acids Research* 17: 5913–5922.

LaMantia, G., Maglione, D., Pengue, G., DiCristofano, A., Simeone, A., Lanfrancone, L., and Lania, L. (1991). Identification and characterization of novel human endogenous retroviral sequences preferentially expressed in undifferentiated embryonal carcinoma cells. *Nucleic Acids Research* 19, 1513–1520.

LaMantia, G., Majello, B., DiCristofano, A., Strazzullo, M., Minchiotti, G., and Lania, L. (1992). Identification of regulatory elements within the minimal promoter region of the human endogenous ERV9 proviruses: accurate transcription initiation is controlled by an Inr-like element. *Nucleic Acids Research* 20, 4129–4136.

Lania, L., Di Cristofano, A., Strazzullo, M., Pengue, G., Majello, B., and LaMantia, G. (1992). Structural and functional Organization of the Human Endogenous Retroviral ERV9 Sequences. *Virology* 191, 464–468.

Lenz, J., Celander, D., Crowther, R. L., Patarca, R., Perkins, D. W., & Haseltine, W. A. (1984). Determination of the leukaemogenicity of a murine retrovirus by sequences within the long terminal repeat. *Nature* 308: 467–470.

Li, Q., Powers, P. A., and Smithies, O. (1985). Nucleotide sequence of 16 kilobase pairs of DNA 5' to the human β-globin gene. *J. Biol. Chem.* 260, 14901–14910.

Li., Q., and Starnatoyamnopoulos, G. (1994). Hypersensitive site 5 of the human β Locus Control Region functions as a chromatin insulator. *Blood* 84, 1399–1401.

Long, Q., Li, C., Nechtman, J., Tjia, J., Yoo, J. and Taun, D. (1995). Nucleotide sequence and transcriptional analysis of DNA upstream of hypersensitive site 4 in the human β-globin locus control region. *Blood* 86, 472a.

Lower, R., Lower, J., and Kurth, R. (1996). The viruses in all of us: Characteristics and biological significance of human endogenous retrovirus sequences. *Proc. Natl. Acad. Sci. USA* 93, 5177–5184.

Ludwig, D., Dhen, F., Peterson, S., Nussenzweig, A., Li, G., and Chen, D. (1997). Ku80 gene expression is Sp1-dependent and sensitive to CpG methylation within a novel cis element. *Gene* 199, 181–194.

Merika, M., & Orkin, S. H., (1993). DNA-binding specificity of GATA family transcription factors. *Mol Cell. Biol.* 13, 3999–4010.

Miller, I. and Bieker, J. (1993). A novel, erythroid cell-specific murine transcription factor that binds to the CACCC element and is related to the Kruppel family of nuclear proteins. *Mol. Cell. Biol.* 13, 2776–2786.

Nienhuis, A., Anagnou, N. and Ley, T. (1984). Advances in thalassemia research. *Blood* 63, 738–758.

Orkin, S. H. (1992). GATA-binding transcription factors in hematopoietic cells. *Blood* 80, 575–581.

Poncz, M., Solowiejczyk, D., Harpel, B., Mory, Y., Schwartz, E. and Surrey, S. (1982). Construction of human gene libraries from small amounts of peripheral blood: analysis of beta-like globin genes. *Hemoglobin* 6, 27–36.

Poncz, M., Schwartz, E., Ballantine, M. and Surrey, S. (1983). Nucleotide sequence analysis of the δβ-globin gene region in human. *J. Biol. Chem.* 258, 11599–11609.

Sanger, F., Nicklen, S. and Coulson, A. R. (1977). DNA sequencing with chain-terminating inhibitors, *Proc. Natl. Acad. Sci. USA* 74, 5463–5467.

Schulte, A. M., Lai, S., Kurtz, A., Czubayko, F., Riegel, A. T., and Wellstein, A. (1996). Human trophoblast and choriocarcinoma expression of the growth factor pleiotrophin attributable to germ-line insertion of an endogenous retrovirus. *Proc. Natl. Acad. Sci. USA* 93, 14759–14764.

Shen, S., Sligthtom, J. and Smithies, O. (1981). A history of the human fetal globin gene duplication. *Cell.* 26, 191–203.

Sibley, C. and Ahlquist, J. (1987). DNA hybridization evidence of hominoid phylogeny: Results from an expanded data set. *J. Mol. Evol.* 26, 99–121.

Smit, A. (1996). The origin of interspersed repeats in the human genome. *Current Opinion in Genetics and Development.* 6, 743–748. Speck, N. A., Renjifo, B., Golemis, E., Frederickson, T. N., Hartley, J. W., and Hopkins, N. (1990). Mutation of the core or adjacent LVb elements of the Moloney murine leukemia virus enhancer alters disease specificity. *Genes & Development* 4, 233–242.

Stavenhagen, J. B. and Robins, D. M. (1988) An ancient provirus has imposed androgen regulation on the adjacent mouse sex-limited protein gene. *Cell* 55247–254.

Stief, A., Winter, D. M., Stratling, W. H. & Sippel, A. E. (1989). A nuclear DNA-attachment element mediates elevated and position-independent gene activity. *Nature* 341, 343–345.

Strazzullo, M., Majello, B., Lania, L., and LaMantia, G. (1994). Mutational Analysis of the Human Endogenous ERV9 Proviruses Promoter Region. *Virology* 200, 686–695.

Strazzullo, M., Parisi, T., DiCristofano, A., Rocchi, M., LaMantia, G. (1998). Characterization and genomic mapping of chimeric ERV9 endogenous retroviruses-host gene transcripts. *Gene* 206, 77–83.

Suzuki, H., Hosokawa, Y., Toda, H., Nishikimi, M., and Ozawa, T. (1990). Common Protein-binding Sites in the 5'-Flanking Regions of Human Genes for Cytochrome c1 and Ubiquinone-binding Protein. *J. Biol. Chem.* 265, 8159–8163.

Temin, H. (1981) Structure, variation and synthesis of retrovirus long terminal repeat. *Cell* 27, 1–3.

Ting, C., Rosenberg, M., Snow, C., Samuelson, L., and Meisler, M. (1992). Endogenous retroviral sequences are required for tissue-specific expression of a human salivary amylase gene. *Genes & Dev.* 6, 1457–1465.

Tuan, D., Solomon, W., Li., Q., & London, I. M. (1985). The β-globin gene domain in human erythroid cells. *Proc. Natl. Acad. Sci USA* 82, 6384–6388.

Tuan, D., Solomon, W. B., London, I. M. & Lee, D. P. (1989). An erythroid-specific, developmental-stage-independent enhancer far upstream of the human β-like globin genes. *Proc. Natl. Acad. Sci. USA* 86, 2554–2558.

Tuan, D., Oh, Y. D., Venditti, C., Cavellesco, R., LeBoulch, P., Huang, G. and London, I. (1990). A distant erythroid enhancer in the regulation of human globin genes during erythropoiesis. In "Molecular Biology of Hematopoiesis (N. G. Abraham, G. Konwalinka, L. Sachs and C. G. Wiedermanm, eds), Intercept Ltd., England.

Tuan, D., Kong, S., & Hu, K. (1992). Transcription of the hypersensitive site HS 2 enhancer in erythroid cells. *Proc. Natl. Acad. Sci USA* 89, 11219–11223.

Vogel, F. and Motulsky, A. (1986). Human Genetics. pp. 534–538. Publisher: Springer Verlag.

Weber-Benarous, A., Cone, R., London, I. and Mulligan, R. (1988). Retroviral-mediated transfer and expression of human β-globin genes in cultured murine and human erytlroid cells. *J. Biol. Chem.* 263, 6142–6145.

Wickrema, A., Krantz, S., Winklemann, J. and Bondurant, M. (1992). Differentiation and erythropoietin receptor gene expression in human erythroid progenitor cells. *Blood* 80, 1940–49.

Wilkinson, D., Mager, D. and Leong, J. (1994). Endogenous human retroviruses. In "The retroviridae" (J. Levy ed), Vol 3, pp. 465–535, Plenum Press, N.Y.

Yang, R., Fristensky, B., Deutch, A. H., Huang, R. C., Tan, Y. H., Narang, S. A. & Wu, R. (1983). The nucleotide sequence of a new human repetitive DNA consists of eight tandem repeats of 66 base pairs. *Gene* 25:59–66.

Yu, J., Bock, J. H., Slightom, J. L. & Villeponteau, B. (1994). A 5' β-globin matrix-attachment region and the polyoma enhancer together confer position-independent transcription. *Gene* 139, 139–145.

Zucchi, I. and Schlessinger, D. (1992). Distribution of moderately repetitive sequences pTR5 and LF1 in Xq24-q28 human DNA and their use in assembling YAC contigs. *Genomics* 12, 264–275.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 22

<210> SEQ ID NO 1
<211> LENGTH: 1831
<212> TYPE: DNA
<213> ORGANISM: Homo sapiens

<400> SEQUENCE: 1

```
gtattgagag gtgacagcgt gctggcagtc ctcacagccc tcgctcgctc ttggcgcctc      60
ctctgcctgg gctcccacat tggtggcact tgaggagccc ttcagccggc cgctgcactg     120
tgggagccct tttctgggct ggccaaggcc agagccggct ccctcagctt gccaggaggt     180
gtggagggac agacgcgggc aggaaccggg ctgtgcgccg tgcttgaggg agttccgggt     240
gggcatgggc tccgaggacc ccgcactcgg agccgccagc cggcccacc ggccgcgggc      300 agtgagggc ttagcacctg ggccagcagc tgctgtgctc aattcctcgc cgggccttag      360
ctgccttcct gcggggcagg gctcgggacc tgcagcgcgc catgcctgag cctccccacc    420
ttcatgggct cctgtgcggc ccgagcctcg ccgacgagcg ccgcccctg ctccagggca      480 cccagtccca tcgaccaccc aagggctgaa gagtgcgggc gccagcaagg ggactggcag     540
gcagctcccc ctgcagccca ggtgcgggat ccactgggtg aagccggcta ggtcctgagt     600
ttgctgggga tgcgaagaac ccttatgtct agataaggga ttgtaaatac accaattggc     660
actctgtatc tagctcaagg tttgtaaaca caccaatcag caccctgtgt ctagctcagg     720
gtttgtgaat gcaccaatca acactctatc tagctactct ggtggggcct tggagaacct    780
```

-continued

| | |
|---|---|
| ttatgtctag ctcagggatt gtaaatacac caatcggcag tctgtatcta gctcaaggtt | 840 |
| tgtaaacaca ccaatcagca ccctgtgtct agctcagggt ttgtgaatgc accaatcaac | 900 |
| actctgtatc tagctactct ggtggggacg tggagaacct ttatgtctag ctcagggatt | 960 |
| gtaaatacac cactcggcag tctgtatcta gctcaaggtt tgtaaacaca ccaatcagca | 1020 |
| ccctgtgtct agctcagggt tgtgaatgc accaatcaac actctgtatc tagctactct | 1080 |
| ggtgggactt ggagaacctt tgtgtggaca ctctgtatct agctaatctg gtggggacgt | 1140 |
| ggagaacctt tgtgtctagc tcatggattg taaatgcacc aatcagtgcc ctgtcaaaac | 1200 |
| agaccactgg gctctctacc aatcagcagg atgtgggtgg ggccagataa gagaataaaa | 1260 |
| gcaggctgcc cgagccagca gtggcaaccc gctcgggtcc ccttccacac tgtggaagct | 1320 |
| ttgttctttc gctctttgca ataaatcttg ctgctgctca ctgtttgggt ctacactgcc | 1380 |
| tttatgagct gtaacgctca ccgcgaaggt ctgcagcttc actcttgaag ccagcgagac | 1440 |
| cacgaaccca ccggaggaac gaacaactcc agaggcgccg cttaagagct ggaacgttca | 1500 |
| ctgtgaaggt ctgcagcttc actcctgagc cagcgagacc acgaaccat cagaaggaag | 1560 |
| aactcgaaca catccaaaca tcagaacgaa caactccaca cacgcagcct ttaagaactg | 1620 |
| taacactcac cacgagggtc cccggcttca ttcttgaagt cagtgaaacc aagaacccac | 1680 |
| caattccgga cacagtatgt cagaaacaat atgagtcact aaatcaatat acttctcaac | 1740 |
| aacagccctt gcaattaact tggccatgtg actggttgtg actaaaataa tgtggagata | 1800 |
| ataatgtgtt actccctaag gcagagtgcc c | 1831 |

<210> SEQ ID NO 2
<211> LENGTH: 103
<212> TYPE: DNA
<213> ORGANISM: Homo sapiens

<400> SEQUENCE: 2

| | |
|---|---|
| tcaaaacgga ccaataagct ctctgtaaaa tgggccaatc agcaggatgt gggtggggtc | 60 |
| agataaggaa ataaaagcag gctgccagag ccagctgtga caa | 103 |

<210> SEQ ID NO 3
<211> LENGTH: 87
<212> TYPE: DNA
<213> ORGANISM: Homo sapiens

<400> SEQUENCE: 3

| | |
|---|---|
| tcaaaccact cggctctacc aatcagcagg atgtgggtgg ggccagataa gagaataaaa | 60 |
| gcaggctgcc cgagccagca gtggcaa | 87 |

<210> SEQ ID NO 4
<211> LENGTH: 105
<212> TYPE: DNA
<213> ORGANISM: Artificial Sequence
<220> FEATURE:
<223> OTHER INFORMATION: Epsilon 1.4 phage

<400> SEQUENCE: 4

| | |
|---|---|
| gacacaggtc agccttgacc aatgactttt aagtaccatg gagaacaggg ggccagaatt | 60 |
| cggcagtaaa gaataaaagg ccagacagag aggcagcagc acata | 105 |

<210> SEQ ID NO 5
<211> LENGTH: 1091
<212> TYPE: DNA
<213> ORGANISM: Artificial Sequence

```
<220> FEATURE:
<223> OTHER INFORMATION: Consensus Sequence
<221> NAME/KEY: misc_feature
<222> LOCATION: (437)..(437)
<223> OTHER INFORMATION: n = any nucleotide

<400> SEQUENCE: 5
tatgtctaga taagggattg taaatacacc aattggcact ctgtatctag ctcaaggttt      60
gtaaacacac caatcagcac cctgtgtcta gctcagggtt tgtgaatgca ccaatcaaca     120
ctctatctag ctactctggt ggggccttgg agaaccttta tgtctagctc agggattgta     180
aatacaccaa tcggcagtct gtatctagct caaggtttgt aaacacacca atcagcaccc     240
tgtgtctagc tcagggtttg tgaatgcacc aatcaacact ctgtatctag ctactctggt     300
ggggacgtgg agaaccttta tgtctagctc agggattgta aatacaccac tcggcagtct     360
gtatctagct caaggtttgt aaacacacca atcagcaccc tgtgtctagc tcagtatcta     420
gctaatctgg tggggangtg gagaaccttt gtgtctagct catggattgt aaatgcacca     480
atcagtgccc tgtcaaaaca gaccactggg ctcttaccaa tcagcaggat gtgggtgggg     540
ccagataaga gaataaaagc aggctgcccg agccagcagt ggcaacccgc tcgggtcccc     600
ttccacactg tggaagcttt gttctttcgc tctttgcaat aaatcttgct gctgctcact     660
gtttgggtct acactgcctt tatgagctgt aacgctcacc gcgaaggtct gcagcttcac     720
tcttgaagcc agcgagacca cgaacccacc gggaggaacg aacaactcca gaggcgccgc     780
cttaagagct ggaacgttca ctgtgaaggt ctgcagcttc actcctgagc cagcgagacc     840
acgaacccat cagaaggaag aaactccgaa cacatccaaa catcagaacg aacaaactcc     900
acacacgcag cctttaagaa ctgtaacact caccacgagg gtccccggct tcattcttga     960
agtcagtgaa accaagaacc caccaattcc ggacacagta tgtcagaaac aatatgagtc    1020
actaaatcaa tatacttctc aacaatttcc aacagccctt gcaattaact tggccatgtg    1080
actggttgtg a                                                         1091

<210> SEQ ID NO 6
<211> LENGTH: 1043
<212> TYPE: DNA
<213> ORGANISM: Homo sapiens

<400> SEQUENCE: 6
tatgtctacc ataagggatt gtaaatacac caattggcac tctgtatcta gctcaaggtt      60
tgtaaacaca ccaatcagca ccctgtgtct agctcagggt ttgtgaatgc accaatcaac     120
actctatcta gctactctgg tggggccttg gagaaccttt atgtctagct cagggattgt     180
aaatacacca atcggcagtc tgtatctagc tcaaggtttg taaacacacc aatcagcacc     240
ctgtgtctag ctcagggttt gtgaatgcac caatcaacac tctgtatcta gctactctgg     300
tggggacgtg gagaaccttt atgtctagct cagggattgt aaatacacca ctcggcagtc     360
tgtatctagc tcaaggtttg taaacacacc aatcagcacc ctgtgtctag ctcatggatt     420
gtaaatgcac caatcagtgc cctgtcaaaa cagaccactg gctctaccaa tcagcagga     480 tgtgggtggg gccagataag agaataaaag caggctgccc gagccagcag tggcaacccg     540
ctcgggtccc cttccacact gtggaagctt tgttctttcg ctctttgcaa taaatcttgc     600
tgctgctcac tgtttgggtc tacactgcct ttatgagctg taacgctcac cgcgaaggtc     660
tgcagcttca ctcttgaagc cagcgagacc acgaacccac cgggaggaac gaacaactcc     720
agaggcgccg ccttaagagc tggaacgttc actggtaaag gtctgcagct tcactcctga     780
```

```
gccagcgaga ccacgaaccc atcagaagga agaaactccg aacacatcca aacatcagaa      840
cgaacaaact ccacacacgc agcctttaag aactgtaaca ctcaccacga gggtccccgg      900
cttcattctt gaagtcagtg aaaccaagaa cccaccaatt ccggacacag tatgtcagaa      960
acaatatgag tcactaaatc aatatacttc tcaacaattt ccaacagccc ttgcaattaa     1020
cttggccatg tgactggttg tga                                             1043
```

<210> SEQ ID NO 7
<211> LENGTH: 801
<212> TYPE: DNA
<213> ORGANISM: Gorilla gorilla

<400> SEQUENCE: 7

```
tatgtctaga taagggattg taaatacacc aattggcact ctgtatctag ctcaaggttt       60
gtaaacacac caatcagcac cctgtgtcta gctcagggtt tgtgaatgca ccaatcaaca      120
ctctgtatct agctaatctg gtggggaagt ggagaacctt tgtgtctagc tcagggattg      180
taaacgcacc aatcagcacc ctgtcaaaac agaccactgg gctctaccaa tcagcaggat      240
gtgggtgggg ccagataaga gaataaaagc aggctgccca agccagcagt ggcaacgtgc      300
tcaggtcccc ttccacactg cggaagcttt gttctttcgc tctttgcaat aaatcttgct      360
gctgctcact gtttgggtct acactgcctt tacgagctat aacgctcacc cgaaggtctg      420
cagcttcact cttgaagcca gcgagaccac gaacccactg ggaggaacga caactccag      480 acgcaccgcc ttaagagctg aacgttcac tgtgaaggtc tgcagcttca ctcctgagcc      540
agcgagacca cgaacccatc agaaggaaga aactccgaac acatccaaac atcagaacga      600
acaaactcca cacgcagc ctttaagaac tgtaacactc accacgaggg tcccgcggct      660
tcattcttga agtcagtga aaccaagaac ctaccaattc ggacacagta tgtcagaaac      720
aatatgagtc actaaatcaa tatacttctc aacaatttcc aacagccctt gcaattaact      780
tggccatgtg actggttgtg a                                                801
```

<210> SEQ ID NO 8
<211> LENGTH: 41
<212> TYPE: DNA
<213> ORGANISM: Homo sapiens

<400> SEQUENCE: 8

```
tatctagctc agggattgta aatacaccaa tcggcagtct g                           41
```

<210> SEQ ID NO 9
<211> LENGTH: 41
<212> TYPE: DNA
<213> ORGANISM: Homo sapiens

<400> SEQUENCE: 9

```
tgtctagctc aaggtttgta aacacaccaa tcagcaccct g                           41
```

<210> SEQ ID NO 10
<211> LENGTH: 41
<212> TYPE: DNA
<213> ORGANISM: Homo sapiens

<400> SEQUENCE: 10

```
tatctagctc agggtttgtg aatgcaccaa tcaacactct g                           41
```

<210> SEQ ID NO 11

```
<211> LENGTH: 37
<212> TYPE: DNA
<213> ORGANISM: Homo sapiens

<400> SEQUENCE: 11
tgtctagcta ctctggtggg gacgtggaga accttta                              37

<210> SEQ ID NO 12
<211> LENGTH: 41
<212> TYPE: DNA
<213> ORGANISM: Artificial Sequence
<220> FEATURE:
<223> OTHER INFORMATION: Consensus Sequence

<400> SEQUENCE: 12
trtctagctc adggtttgtr aayrcaccaa tcagcactct g                         41

<210> SEQ ID NO 13
<211> LENGTH: 41
<212> TYPE: DNA
<213> ORGANISM: Artificial Sequence
<220> FEATURE:
<223> OTHER INFORMATION: Consensus Sequence

<400> SEQUENCE: 13
tgtctagctm aaggtttgta aatgcaccaa tcagcactct g                         41

<210> SEQ ID NO 14
<211> LENGTH: 41
<212> TYPE: DNA
<213> ORGANISM: Artificial Sequence
<220> FEATURE:
<223> OTHER INFORMATION: Consensus Sequence

<400> SEQUENCE: 14
trtctagctm arggwttgta aacrcaccaa tcagcactct g                         41

<210> SEQ ID NO 15
<211> LENGTH: 31
<212> TYPE: DNA
<213> ORGANISM: Artificial Sequence
<220> FEATURE:
<223> OTHER INFORMATION: Oligonucleotide

<400> SEQUENCE: 15
actgtcgaca agcttctgac aaattattct t                                    31

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide

<400> SEQUENCE: 16
gatggatcca ctgaaagggc tcatgcaac                                       29

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide

<400> SEQUENCE: 17
ctgagtttgc tggggatgcg aa                                              22
```

```
<210> SEQ ID NO 18
<211> LENGTH: 26
<212> TYPE: DNA
<213> ORGANISM: Artificial Sequence
<220> FEATURE:
<223> OTHER INFORMATION: Oligonucleotide

<400> SEQUENCE: 18
gatttagtga ctcatattgt ttctga                                          26

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide

<400> SEQUENCE: 19
tgctgctgct cactgtttgg gtcta                                           25

<210> SEQ ID NO 20
<211> LENGTH: 25
<212> TYPE: DNA
<213> ORGANISM: Artificial Sequence
<220> FEATURE:
<223> OTHER INFORMATION: Oligonucleotide

<400> SEQUENCE: 20
gggcactctg ccttagggag taaca                                           25

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide

<400> SEQUENCE: 21
actgtcgact tatgtattca agttcg                                          26

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide

<400> SEQUENCE: 22
gatggatcca atagattttt gtcatct                                         27
```

We claim:

1. An isolated nucleic acid molecule comprising a U3 enhancer defined by nucleotides 595 to 1193 of SEQ ID NO:1, or a fragment thereof, wherein the nucleic acid molecule or fragment exhibits U3 enhancer function.

2. The isolated nucleic acid molecule of claim 1 further comprising nucleotides 5 to 594 of SEQ ID NO:1 operably linked to the enhancer.

3. The isolated nucleic acid molecule of claim 1 further comprising the U3 promoter defined by nucleotides 1194 to 1322 of SEQ ID NO:1 operably linked to the enhancer.

4. The isolated nucleic acid molecule of claim 1 further comprising the U3 R region defined by nucleotides 1322 to 1380 of SEQ ID NO:1 operably linked to the enhancer.

5. The isolated nucleic acid molecule of claim 1 further comprising a gene operably linked to the enhancer.

6. The isolated nucleic acid molecule of claim 5 wherein the gene encodes a protein.

7. A vector comprising the nucleic acid molecule of claim 6.

8. A method of expressing a protein in vitro, the method comprising culturing a cell transformed with the vector of claim 7, wherein the protein encoded by the gene is expressed.

9. A method for introducing DNA into the genome of a cultured cell, the method comprising introducing the vector of claim 7 into the cultured cell, wherein the gene is expressed.

10. A vector comprising the nucleic acid molecule of claim 5.

11. The vector of claim 10 wherein the vector is a retroviral vector.

12. An isolated cell transformed with the vector of claim 10.

13. The isolated cell of claim 12 wherein the cell is a mammalian cell.

14. The isolated cell of claim 12 wherein the cell is an animal cell.

15. The isolated cell of claim 12, wherein the cell is an embryonic cell.

16. A method for introducing DNA into the genome of a cultured cell, the method comprising introducing the vector of claim 10 into the cultured cell, wherein the gene is expressed.

17. An isolated nucleic acid molecule comprising a U3 insulator comprising nucleotides 5 to 594 of SEQ ID NO:1, wherein the nucleic acid molecule exhibits U3 insulator function.

18. The isolated nucleic acid molecule of claim 17 further comprising nucleotides 1194 to 1322 of SEQ ID NO:1 operably linked to the insulator.

19. The isolated nucleic acid molecule of claim 17 further comprising nucleotides 1322 to 1380 of SEQ ID NO:1 operably linked to the insulator.

20. The isolated nucleic acid molecule of claim 17 further comprising a gene operably linked to the insulator.

21. The isolated nucleic acid molecule of claim 20 wherein the gene encodes a protein.

22. A vector comprising the nucleic acid molecule of claim 21.

23. A method of expressing a protein in vitro, the method comprising culturing a cell transformed with the vector of claim 22, wherein the protein encoded by the gene is expressed.

24. A method for introducing DNA into the genome of a cultured cell, the method comprising introducing the vector of claim 22 into the cultured cell, wherein the gene is expressed.

25. A vector comprising the nucleic acid molecule of claim 20.

26. The vector of claim 25 wherein the vector is a retroviral vector.

27. An isolated cell transformed with the vector of claim 25.

28. The isolated cell of claim 27 wherein the cell is a mammalian cell.

29. The isolated cell of claim 27 wherein the cell is an animal cell.

30. A method for introducing DNA into the genome of a cultured cell, the method comprising introducing the vector of claim 22 into the cultured cell, wherein the gene is expressed.

31. The isolated nucleic acid of claim 17, wherein said U3 insulator functions to protect the nucleic acid molecule against instability due to position effects upon insertion of said nucleic acid into a genome.

32. An isolated nucleic acid molecule comprising an enhancer, wherein the enhancer has five or more repeats, wherein each repeat comprises one of the following sequences:

TRTCTAGCTCADGGTTTGTRAAYRCAC-CAATCAGCACTCTG (SEQ ID NO:12),
TATCTAGCTCAGGGATTGTAAATACAC-CAATCGGCAGTCTG (SEQ ID NO: 8),
TGTCTAGCTCAAGGTTTGTAAACACAC-CAATCAGCACCCTG (SEQ ID NO: 9),
TATCTAGCTCAGGGTTTGTGAATGCAC-CAATCAACACTCTG (SEQ ID NO: 10),
TGTCTAGCTACTCTGGTGGGGACGTG-GAGAACCTTTA (SEQ ID NO: 11).

33. The isolated nucleic acid molecule of claim 32, wherein each repeat comprises one of the following sequences:

TATCTAGCTCAGGGATTGTAAATACAC-CAATCGGCAGTCTG (SEQ ID NO: 8),
TGTCTAGCTCAAGGTTTGTAAACACAC-CAATCAGCACCCTG (SEQ ID NO: 9),
TATCTAGCTCAGGGTTTGTGAATGCAC-CAATCAACACTCTG (SEQ ID NO: 10),
TGTCTAGCTACTCTGGTGGGGACGTG-GAGAACCTTTA (SEQ ID NO: 11).

34. The isolated nucleic acid molecule of claim 32, wherein each repeat comprises the following sequence:
TRTCTAGCTCADGGTTTGTRAAYRCAC-CAATCAGCACTCTG (SEQ ID NO:12).

35. The isolated nucleic acid molecule of claim 32, wherein the enhancer comprises from five to fourteen repeat units.

36. The isolated nucleic acid molecule of claim 32, wherein the enhancer is a primate 5' HS5 ERV-9 LTR enhancer.

* * * * *

UNITED STATES PATENT AND TRADEMARK OFFICE
CERTIFICATE OF CORRECTION

PATENT NO.   : 6,395,549 B1
DATED        : May 28, 2002
INVENTOR(S)  : Dorothy Tuan et al.

It is certified that error appears in the above-identified patent and that said Letters Patent is hereby corrected as shown below:

<u>Title page</u>
Item [56], OTHER PUBLICATIONS, "Anderson et al., (*Virology* 234:14-30 (1997)," please correct the author's name, "Anderson" to read -- Anderssen --
"Anderson et al., (*Virology* 234:14-30 (1997)," please correct the word "retrpvirus" to read -- retrovirus --
Please insert the following articles:
-- Anderson, "Human Gene Therapy," *Science*, 256:808-813 (1992) --
-- Anderson, et al., "The ADA Human Gene Therapy Clinical Protocol," *Hum. Gen. Ther.*, 1:331-362 (1990) --
Fuechter-Murthy, et al., "Splicing of a human endogenous retrovirus to a novel phospholipase A2 related gene," *Nucleic Acids Research*, 21:135-143 (1993) --
"Ashe, et al.," reference, please correct the word "transiduction" to read
-- transinduction --
"Buchschacher, et al.," reference, please correct the word "innunodoficiency" to read -- immunodeficiency -- and the word "Viral." to read -- Virol. --
"Dicristofano, et al.," reference, please correct the word ""zing-finger" to read
-- zinc-finger --
"Dhar, et al.," reference, please correct the word "Erthroid" to read
-- Erythroid -- and the word "domaine" to read -- domain --
"Golemis, et al.," reference, please correct the word "Virusis" to read -- Viruses -- and the word "impications" to read -- implications --
"Goodchild, et al.," reference, please correct the word "endogienous" to read
-- endogenus -- and the word "erpeat" to read -- repeat --
"Grosveld, et al., reference, please correct the word "tragenic" to read -- transgenic --
"Jarman & Higgs," reference, please correct the word "complese" to read
-- complexes --
"Johnson & McKnight," reference, please correct the year "1989(" to read -- (1989) --
"Kesher, et al.," reference, please correct the author's name "Kesher" to read
-- Keshet --, please correct the word "resservoir" to read -- reservoir -- and the word "specificitis" to read -- specificities --
"Khoury & Gruss," reference, please correct the cite "33(2):13-4 (1983)" to read
-- 33(2):313-4 (1983) --
"Lenz, et al.," reference, please correct the word "muring" to read -- murine --
"Orkin," reference, please correct the word "Blooed" to read -- *Blood* --
"Speck, et al.," reference, please correct the word "Monioney" to read
-- Moloney --
"Stavenhagen & Robins," reference, please correct the word "Ana" to read
-- An -- and the word "prvirus" to read -- provirus --
"Stief, et al.," reference, please correct the word "Anuclear" to read -- A nuclear --
"Tolstoshev," reference, please correct the word "Toicol." to read -- Toxicol. --

UNITED STATES PATENT AND TRADEMARK OFFICE
CERTIFICATE OF CORRECTION

PATENT NO.     : 6,395,549 B1
DATED          : May 28, 2002
INVENTOR(S)    : Dorothy Tuan et al.

It is certified that error appears in the above-identified patent and that said Letters Patent is hereby corrected as shown below:

"Zucchi & Schlessinger," reference, please correct the sequence "Xq24-q-28" to read -- Xq24-q28 --

Column 10,
Line 23, please correct the word "MRNA" to read -- mRNA --
Line 34, please correct the word "famnilial" to read -- familial --
Line 48, please correct the cite "Ann. Rev. Biochem, 62:191 (1992) to read -- Ann. Rev. Biochem. 62:191 (1993) --

Column 12,
Line 35, please correct the word "erytiroid" to read -- erythroid --

Column 13,
Line 50, please correct the word "subdones" to read -- subclones --

Column 14,
Lines 10 thru 13, please remove the periods after each Celsius symbol "C." to read -- PCR conditions consist of an initial denaturation at 95° C for 1.5 min, followed by 32 cycles of denaturation at 95° C for 1.5 min, annealing at 59° C for 1min and extension at 72° C for 15 min. --

Column 17,
Line 50, please correct the word "genoniic" to read -- genomic --

Column 23,
Line 39, please correct the spelling of the name "Starnatoyamnopoulos" to read -- Stamatoyamnopoulos --

UNITED STATES PATENT AND TRADEMARK OFFICE
CERTIFICATE OF CORRECTION

PATENT NO. : 6,395,549 B1
DATED : May 28, 2002
INVENTOR(S) : Dorothy Tuan et al.

It is certified that error appears in the above-identified patent and that said Letters Patent is hereby corrected as shown below:

Columns 35 and 36,
Sequence Listing, insert SEQ ID Nos: 23, 24 and 25 as follows:

```
<400>  23
tactgtcgac ctgagtttgc tggggatg                                       28

<210>  24

<211>  27

<212>  DNA

<213>  Artificial Sequence

<220>

<223>  Oligonucleotide

<400>  24
gatggatcct gtgtccggaa ttggtgg                                        27

<210>  25

<211>  1165

<212>  DNA

<213>  Homo sapien

<400>  25
tatgtctaga taagggattg taaatacacc aattggcact ctgtatctag ctcaaggttt    60
gtaaacacac caatcagcac cctgtgtcta gctcagggtt tgtgaatgca ccaatcaaca   120
ctctatctag ctactctggt ggggccttgg agaacctttA tgtctagctc agggattgta   180
aatacaccaa tcggcagtct gtatctagct caaggtttgt aaacacacca atcagcaccc   240
tgtgtctagc tcagggtttg tgaatgcacc aatcaacact ctgtatctag ctactctggt   300
ggggacgtgg agaacctttA tgtctagctc agggattgta aatacaccac tcggcagtct   360
gtatctagct caaggtttgt aaacacacca atcagcaccc tgtgtctagc tcagggtttg   420
tgaatgcacc aatcaacact ctgtatctag ctactctggt gggacttgga gaacctttgt   480
gtggacactc tgtatctagc taatctggtg gggacgtgga gaacctttgt gtctagctca   540
tggattgtaa atgcaccaat cagtgccctg tcaaaacaga ccactgggct ctctaccaat   600
cagcaggatg tgggtggggc cagataagag aataaaagca ggctgcccga gccagcagtg   660
gcaacccgct cgggtcccct tccacactgt ggaagctttg ttctttcgct ctttgcaata   720
aatcttgctg ctgctcactg tttgggtcta cactgccttt atgagctgta acgctcaccg   780
cgaaggtctg cagcttcact cttgaagcca gcgagaccac gaacccaccg gaggaacgaa   840
```

UNITED STATES PATENT AND TRADEMARK OFFICE
CERTIFICATE OF CORRECTION

PATENT NO.    : 6,395,549 B1
DATED         : May 28, 2002
INVENTOR(S)   : Dorothy Tuan et al.

It is certified that error appears in the above-identified patent and that said Letters Patent is hereby corrected as shown below:

```
caactccaga ggcgccgctt aagagctgga acgttcactg tgaaggtctg cagcttcact    900
cctgagccag cgagaccacg aacccatcag aaggaagaac tcgaacacat ccaaacatca    960
gaacgaacaa ctccacacac gcagccttta agaactgtaa cactcaccac gagggtcccc   1020
ggcttcattc ttgaagtcag tgaaaccaag aacccaccaa ttccggacac agtatgtcag   1080
aaacaatatg agtcactaaa tcaatatact tctcaacaat ttccaacagc ccttgcaatt   1140
aacttggcca tgtgactggt tgtga                                         1165
```

<u>Column 38,</u>
Line 5, please correct "claim 22" to read -- claim 25 --

Signed and Sealed this

Fifteenth Day of July, 2003

JAMES E. ROGAN
*Director of the United States Patent and Trademark Office*